(12) United States Patent
Ricci et al.

(10) Patent No.: US 11,168,114 B2
(45) Date of Patent: Nov. 9, 2021

(54) PROCESS FOR THE MANUFACTURE OF DEGARELIX AND ITS INTERMEDIATES

(71) Applicant: Fresenius Kabi iPSUM S.r.l, Milan (IT)

(72) Inventors: Antonio Ricci, Milan (IT); Jacopo Zanon, Milan (IT); Walter Cabri, Milan (IT); Ivan Guryanov, Padua (IT); Andrea Orlandin, Cazarzere (IT); Barbara Biondi, Venezia-Mestre (IT); Fernando Formaggio, Noventa Vicentina (IT); Dario Visentini, Villadose (IT)

(73) Assignee: FRESENIUS KABI IPSUM S.R.L, Milan (IT)

( * ) Notice: Subject to any disclaimer, the term of this patent is extended or adjusted under 35 U.S.C. 154(b) by 316 days.

(21) Appl. No.: 16/062,278

(22) PCT Filed: Dec. 19, 2016

(86) PCT No.: PCT/EP2016/081784
§ 371 (c)(1),
(2) Date: Jun. 14, 2018

(87) PCT Pub. No.: WO2017/103275
PCT Pub. Date: Jun. 22, 2017

(65) Prior Publication Data
US 2018/0362588 A1  Dec. 20, 2018
US 2020/0172577 A9  Jun. 4, 2020

(30) Foreign Application Priority Data
Dec. 17, 2015  (EP) .................................... 15200832

(51) Int. Cl.
*C07K 7/23* (2006.01)
(52) U.S. Cl.
CPC ..................................... *C07K 7/23* (2013.01)
(58) Field of Classification Search
None
See application file for complete search history.

(56) References Cited

U.S. PATENT DOCUMENTS 5,925,730 A    7/1999  Semple et al.

FOREIGN PATENT DOCUMENTS

| CN | 102952174 A | 3/2013 |
| CN | 103992392 A | 8/2014 |
| WO | WO 1998-46634 * | 1/1998 |
| WO | 1998046634 A1 | 10/1998 |
| WO | WO 1999-26964 * | 1/1999 |
| WO | 1999026964 A1 | 6/1999 |
| WO | 2010121835 A1 | 10/2010 |
| WO | 2011066386 A1 | 6/2011 |

OTHER PUBLICATIONS

International Search Report and Written Opinion for International Application PCT/EP2016/081784 dated Feb. 28, 2017, 13 pgs.
Jiang et al., GnRH Antagonists: A New Generation of Long Acting Analogues Incorporating p-Ureido-phenylalanines at Positions 5 and 6t, J. Med. Chem. 2001, 44, 453-467.
Kaplanek et al., Fast and effective reduction of nitroarenes by sodium dithionite under PTC conditions: application in solid-phase synthesis, Tetrahedron Letters 54 (2013) 2600-2603.
Samant et al., Synthesis, in vivo and in vitro biological activity of novel azaline B analogs, Bioorganic & Medicinal Chemistry Letters 15 (2005) 2894-2897.
Steinberg, Degarelix: A Gonadotropin-Releasing Hormone Antagonist for the Management of Prostate Cancer, Clinical Therapeutics/vol. 31, Theme Issue, 2009, 2312-2331.
Theobald et al., Novel gonadotropin-releasing hormone antagonists: peptides incorporating modified N.omega.-cyanoguanidino moieties, J. Med. Chem. 1991, 34, 2395-2402.

* cited by examiner

*Primary Examiner* — James H Alstrum-Acevedo
*Assistant Examiner* — Tara L Martinez
(74) *Attorney, Agent, or Firm* — Hylton-Rodic Law PLLC

(57) ABSTRACT

The present invention provides a manufacturing process for preparing a peptide, preferably a decapeptide, such as degarelix, by incorporating p-nitro-phenylalanin in the amino acid sequence preferably during stepwise solid phase synthesis, and converting these into the required amino acids Aph(Hor) and/or D-Aph(Cbm), preferably while attached to a solid phase. The invention further provides intermediates useful in the manufacturing process.

14 Claims, 4 Drawing Sheets

Pure degarelix

PROCESS FOR THE MANUFACTURE OF DEGARELIX AND ITS INTERMEDIATES

CROSS REFERENCE TO RELATED APPLICATIONS

This application is a U.S. national stage application of International Application No. PCT/EP2016/081784, filed Dec. 19, 2016, which claims the benefit of the filing date of European Application 5200832.2, filed Dec. 17, 2015, the contents of which are hereby incorporated by reference in their entirety.

FIELD OF THE INVENTION

The present invention relates to a process, or method of synthesis, for preparing peptides wherein at least one amino acid in the peptide is characterized as an unnatural aminophenylalanin derivative, specified as Aph(Hor) or Aph(Cbm). In particular the invention relates to the synthesis of decapeptides, such as degarelix, and its protected precursor, and other useful intermediates. Intermediates useful in the manufacturing process are also described. The method of synthesis is characterized by the use of p-nitro-phenylalanine, which is incorporated in the growing peptide chain at the respective positions of Aph(Hor) and/or D-Aph(Cbm) in the final peptide sequence. Another method of synthesis is based on the use of a compound of Formula II, which is itself synthesized by the use of p-nitro-phenylalanine.

BACKGROUND OF THE INVENTION

The synthesis of peptides carrying at least one aminophenylalanin derivative, such as for example Aph(Hor), Aph(Cbm) or Aph (Atz) in their amino acid sequence is challenging. The synthesis often results in a product with a high amount of impurities (such as deletion products or products of side reactions).

WO99/26964 is addressing the problem of synthesizing azaline B, a decapeptide that carries two identical unnatural amino acids Aph(Atz) at positions 5 and 6. The suggested synthesis starts with synthesizing of the central "5/6" dipeptide fragment. The core of this method is the simultaneous incorporation of both aminotriazole groups (Atz=5-(3'-amino-1H-1',2',4'-triazolyl). First, a nitro-substituted Phe-Phe dipeptide is generated. The nitro groups on the dipeptide are then reduced to obtain the amino substituted dipeptide. The 1,2,4-triazole groups are then formed simultaneously on the amino-substituted phenylalanine groups by reacting the reduced dipeptide first with diphenyl cyanocarbonimidate and then with hydrazine. The final "5/6" dipeptide fragment is obtained by reaction with a suitable base and then reacted with the missing fragments in a liquid reaction. Obviously this elegant approach is not suitable for the synthesis of decapeptides with different Aph side chains, such as degarelix. Furthermore, it is not possible to be performed as solid state peptide synthesis, but as liquid phase synthesis only. In WO99/26964 the solid state synthesis is regarded unsuitable for providing an improved synthesis of degarelix (page 7).

It remains a challenging task to efficiently synthesize peptides with different derivatives of Aph in their 5 and 6 position.

U.S. Pat. No. 5,925,730 discloses a selection of decapeptides, which have GnRH antagonistic properties and may be used for treatment. All of these antagonists have a derivative of Aph in the 5- and/or 6-positions. They are depicted by the generic sequence X-D-2Nal-(A)D-Phe-D-3Pal-Ser-Xaa5-Xaa6-Leu-Xaa8-Pro-Xaa10, wherein Xaa5 is 4Aph(Q1) or 4Amf(Q1) with Q1 being D- or L-Hor or D- or L-Imz, and Xaa6 is D-4Aph(Q2), D-4Amf(Q2), with Q2 being For, Ac, 3-amino-1,2,4 triazole, or Q1. Alternatively, when Xaa6 contains Q, wherein Q is

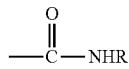

or D- or L-Hor or D- or L-Imz, Xaa5 may have Ac, For or 3-amino-1,2,4-triazole as Q1.

The Aph derivative may contain a carbamoyl group or a heterocycle including a urea in its side chain, for example Ac-D-2Nal-D-4Cpa-D-3Pal-Ser-4Aph(hydroorotyl)-D-4Aph(acetyl)-Leu-Lys(isopropyl)-Pro-D-Ala-NH2, and Ac-D-2Nal-D-4Cpa-D-3Pal-Ser-4Aph(hydro-orotyl)-D-4Amf(Q2)-Leu-Lys(isopropyl)-Pro-D-Ala-NH2, wherein Q2 is Cbm or MeCbm. The most prominent example of such a peptide is the decapeptide degarelix. Degarelix, is an approved medicinal product.

In the following an improved synthesis of peptides with Aph derivatives, such as for example Aph(Hor) or Aph (Cbm), in their sequence, is disclosed that results in a product of high yield and purity without the need to invest in the production or procurement of specialty amino acids, such as Aph(Hor) or Aph(Cbm). A synthesis for degarelix is also disclosed.

The compound Ac-D-Nal-D-Cpa-D-Pal-Ser-Aph(Hor)-D-Aph(Cbm)-Leu-Lys(iPr)-Pro-D-Ala-NH$_2$, also known as degarelix is represented by the Formula (I), the numbers indicate the direction of counting the relevant amino acid positions:

Formula I

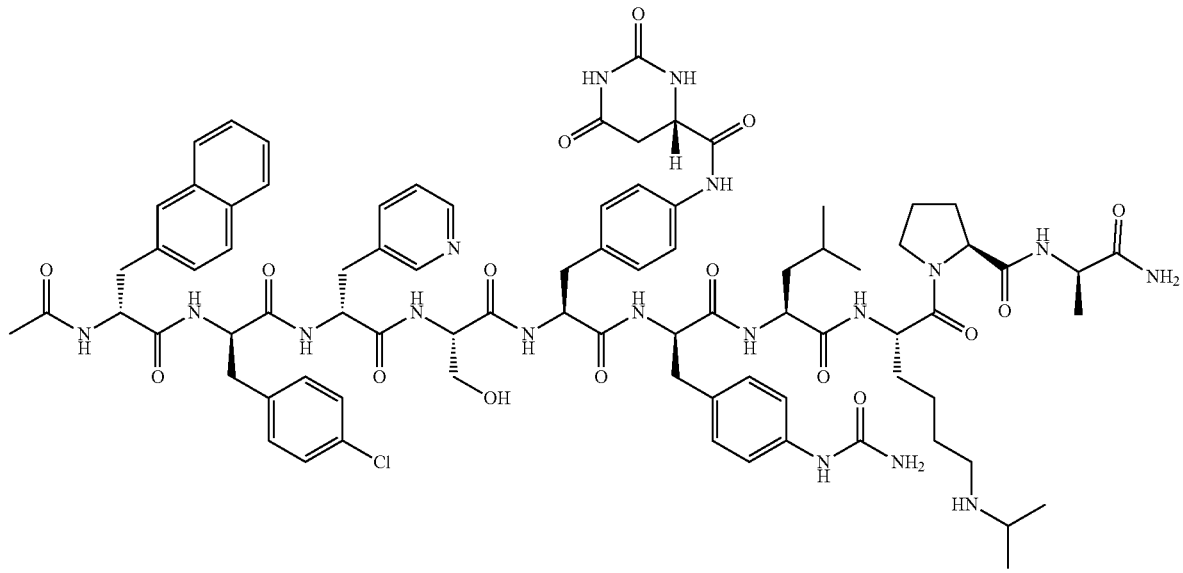

Degarelix (a pharmaceutical composition thereof is marketed under the trade name Firmagon®), also known as FE200486 is a synthetic linear decapeptide and a third generation gonadotropin releasing hormone (GnRH) receptor antagonist (a GnRH blocker). It was approved by the U.S. Food and Drug Administration (FDA) on 24 Dec. 2008 for treatment of patients with advanced prostate cancer. It acts by decreasing the level of luteinizing hormone and suppressing testosterone and prostate-specific antigen (PSA) secretion (G. Jiang et al. J. Med. Chem. 44, 2001, 453-467; M. P. Samant et al. Bioorg Med. Chem. Lett. 15, 2005, 2894-2897). It has a number of advantages over many other GnRH antagonists, such as high affinity and potency at the GnRH receptor, water solubility sufficient for the development of an injectable formulation, as well as properties enabling the development of a sustained release form (M. Steinberg. Clin. Ther. 31, 2009, 2312-2331), which allows to decrease testosterone concentration fast and to maintain this level for an increased amount of time.

Degarelix, as represented by formula I was first reported in international publication no. WO 98/46634. WO 98/46634 describes the synthesis of degarelix using solid phase peptide synthesis (SPPS) on MBHA resin and Boc-Na protection of amino acids. The removal of Boc-protective group after each coupling step was achieved by 50% solution of trifluoroacetic acid in dichloromethane with addition of 1% of m-cresole. D-Aph(Cbm) and L-Aph(Hor) residues were introduced in the peptide structure as D-Aph(Fmoc) and L-Aph(Fmoc) followed by consecutive Fmoc-deprotection by applying a 25% solution of piperidine in dimethylformamide and treatment with t-butyl isocyanate and hydroorotic acid respectively. The completion of SPPS and cleavage of the peptide with hydrogen fluoride resulted in obtaining full-length degarelix. Alternatively, the Fmoc-protective group of Aph in position 5 was removed only after the completion of solid phase synthesis and the peptide eventually modified with L-dihydroorotic acid.

The above mentioned synthetic processes do not result in degarelix of high purity. The processes involve use of hazardous reagents such as hydrogen fluoride. Moreover, the final cleavage of the peptide under very strong acidic conditions induces a partial degradation of the peptide, which causes a significant amount of yield to be lost. Furthermore, the impurity profile achieved by these syntheses requires purification steps which result in higher losses.

In the following years alternative methods suitable for the industrial production of degarelix, several approaches based on SPPS and LPPS, as well as the combination of these methods, were proposed.

WO2010/121835 discloses a method of stepwise Fmoc based SPPS synthesis of full-length degarelix using the two commercially available p-amino phenylalanine derivatives having a carbamoyl moiety and a dihydroorotyl moiety, Aph(Cbm) and Aph(Hor), respectively. These residues were introduced without any modification during a regular SPPS, which comprised only sequential coupling and deprotection steps. Degarelix obtained by this method showed to contain the 4-([2-(5-hydantoyl)]acetylamino)-phenylalanine analog of degarelix, which is known to be formed after dihydroorotic moiety isomerisation in basic conditions, in an amount lower than 0.3%.

Another method based on Fmoc-SPPS is described in WO2011/066386, where the trityl protective group for serine is used, instead of the t-butyl. The use of this more acid-labile protective group allowed to decrease the time of the final cleavage and to get a crude product with a lower amount of impurities. WO2011/066386 also discloses the synthesis of degarelix via a (9+1) condensation strategy and (3+6+1) condensation strategy.

Similarly, a liquid phase condensation process for degarelix preparation was disclosed in WO2012/055903. Various fragments of degarelix were synthesized in solution or on the solid phase and coupled in solution. In particular, [4+6] and [3+7] strategies were described.

Chinese patent application, CN103992392, discloses a method for the synthesis of degarelix by the introduction of Aph(Hor) wherein the base-labile protection group Dde for the p-amino group was used. Its deprotection with 2% hydrazine in dimethylformamide with the following coupling of hydroorotic acid on the solid phase and cleavage from the resin yielded the final crude product.

Chinese patent application, CN102952174, discloses a method for the synthesis of degarelix on the Rink amide resin, wherein Aph(Trt) was introduced during Fmoc-based SPPS. The trityl protection was removed with 10% trifluoroacetic acid. The unprotected amino group was coupled with hydroorotic acid.

All the above mentioned processes include the insertion of Aph derivatives into the structure of degarelix that have to be prepared and purified previously by standard methods of organic chemistry. It complicates the overall synthesis of the peptide. Moreover, the introduction of these bulky residues in the peptide sequence, preferably during a step-by-step solid phase synthesis, is complicated because of their steric hindrance and, therefore may cause difficulties in the coupling steps. These residues (p-amino phenylalanine derivatives Aph(Hor) and D-Aph(Cbm) in particular in the $5^{th}$ and $6^{th}$ position of the decapeptide respectively), can also induce the aggregation of the growing peptide chain due to inter- and intramolecular hydrogen bond formation. All these factors can lead to a noticeable formation of side products, such as, for example, deletion products, i.e. side products formed which are lacking an amino acid of the intended sequence.

The methods known for the preparation of degarelix suffer from one or more of the following drawbacks: low yields obtained due to the formation of side products (deletion products), and unfavorable impurity profiles leading in more losses during purification of the crude peptide, and the need to use hazardous reagents and complicated processes.

Thus, there remains a need to develop an efficient, simple and industrially viable synthetic process which can overcome the drawbacks of the prior art and which provides (crude) peptides, in particular degarelix, in high yield and a favorable impurity profile, facilitating the generation of purified peptides, such as degarelix with high yield and high purity.

Object of the Invention

It is an objective of the present invention to overcome the above-mentioned drawbacks of the prior art.

It is another objective of the present invention to provide an improved process for the synthesis of the decapeptide degarelix or a pharmaceutically acceptable salt thereof without the use of hazardous reagents.

It is another objective of the present invention to provide an improved process for the synthesis of degarelix or a pharmaceutically acceptable salt thereof, which results in crude degarelix in a high yield and an impurity profile facilitating a simplified purification process and/or a significantly higher yield and purity than achieved in the state of the art.

It is a further objective of the present invention to provide useful intermediates for the synthesis of degarelix or a pharmaceutically acceptable salt thereof.

SUMMARY OF THE INVENTION

The present invention provides an improved process for the preparation of peptides, or pharmaceutically acceptable salts thereof, wherein the peptide is characterized as being a peptide with an Aph(Hor) and/or an Aph(Cbm) in the peptide sequence. Preferably the Aph(Hor) and an Aph (Cbm) are the $5^{th}$ and/or $6^{th}$ position. Preferably the peptide is a decapeptide. The most preferred peptide is the decapeptide degarelix, with an Aph(Hor) and an Aph(Cbm) in the $5^{th}$ and $6^{th}$ position, respectively. The process of the present invention results in a crude peptide of higher purity, with high yield, and an improved impurity profile.

The method of synthesis for preparing a peptide, which is characterized as having at least one of, the amino acid Aph(Hor), preferably in the $5^{th}$ position, or the amino acid Aph(Cbm), preferably in the $6^{th}$ position, in its sequence, is characterized by the incorporation of at least one p-nitrophenylalanine into the growing peptide chain. The method preferably comprises the use of the amino acid para-nitrophenylalanine or a nitro-peptide, which is characterized as comprising one or two p-nitrophenylalanine residues. In preferred embodiments these nitro-peptides are the compounds of formula II, formula V, and/or formula VII. The method is further characterized by the steps which subsequently transform the incorporated p-nitrophenylalanin into either Aph(Hor) or Aph(Cbm), as required by the final target peptide sequence. In a another aspect, a synthesis for preparing degarelix of formula I, Formula I

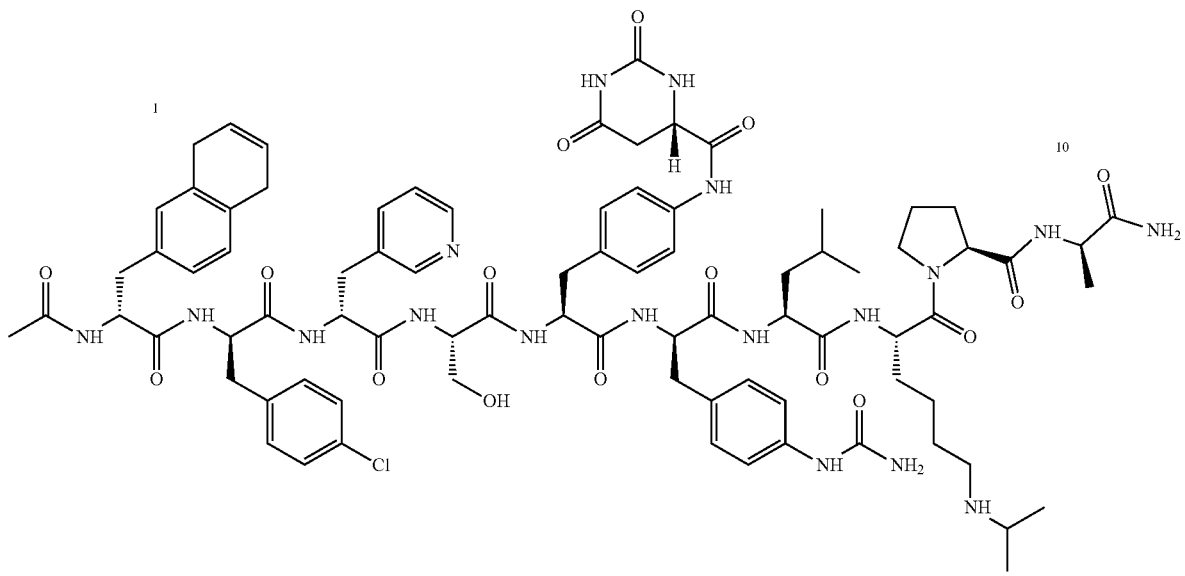

or a pharmaceutically acceptable salt thereof, is provided, wherein the method comprises the use of either the amino acid p-nitrophenylalanine, or a nitro-peptide, which is characterized as comprising one or two p-nitrophenylalanine residues. In preferred embodiments these nitro-peptides are the compounds of formula II, formula V, and formula VII.

A p-nitro-phenylalanine may be incorporated for either the $5^{th}$ or the $6^{th}$ position of degarelix or both, the p-nitrophenylalanine incorporated in the $6^{th}$ position within the degarelix is the D isomeric form, and the p-nitrophenylalanine incorporated in the $5^{th}$ position within the degarelix is the L isomeric form. When L or D is not specifically indicated the L form is referred to.

This may be achieved by introducing p-nitro-phenylalanine instead of the bulkier phenylalanine derivatives known from the art into a precursor peptide, for example by adding a p-nitro-phenylalanine to Leu-Lys(iPr, BOC)-Pro-D-Ala, or to a compound of Formula XI, or to D-Aph(Cbm-tBu)-Leu-Lys(iPr, BOC)-Pro-D-Ala, or to a compound of formula IX. The resulting intermediates may be used to produce degarelix, for example by consecutive reduction to p-amino-phenylalanine and modification thereof.

Due to the difference of the side groups, both Aph amino acid side groups cannot be built up simultaneously, as is possible for azaline B, but instead for example the Aph (Cbm) has to be built first and then has to be protected with a suitable protective group, before the second amino acid side group, for example Aph(Hor) is built up by reduction of the inserted nitro group. One challenge is therefore, to find suitable conditions for these reduction reactions. The inventors found that stannous chloride (Sn(II)Cl$_2$ did work best, under the suitable conditions as indicated below. Thereby they developed an improved synthesis for degarelix.

Preferably the syntheses described herein are performed as solid phase peptide syntheses. Therefore the schemes will show the peptide bound to a "Resin". It is therefore preferred that the "Resin" is a solid support. In principal the same reaction scheme may be performed wherein "Resin" is H, when the synthesis steps are performed in solution.

In solid phase synthesis the protection may be based on the so called BOC protection strategy or the Fmoc protection strategy. More preferably the synthesis is based on the Fmoc protection strategy, wherein the terminal protection group Pg is a base-labile protective group, preferably Fmoc. It is most preferred that all solid state syntheses according to the invention are performed with the Fmoc protection strategy.

Another challenge for such syntheses is the capability to be scaled-up. Usually solid phase syntheses are not ideally suited for scale up. Surprisingly the synthetic approaches described below could be scaled up to a final production yield of at least 0.5 g.

In another aspect, a peptide synthesis for preparing degarelix of formula I, or a pharmaceutically acceptable salt thereof, is provided comprising converting a compound of formula II,

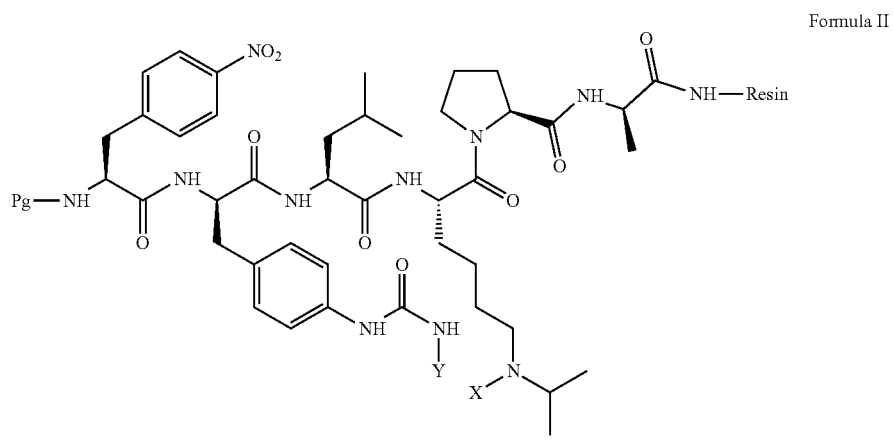

Formula II wherein Pg is a terminal protecting group, X is a side chain protecting group and Y is a side chain protecting group or H, and Resin is a solid support;

into degarelix or a pharmaceutically acceptable salt thereof.

Preferably this synthesis, as well as the synthesis of other peptides according to the invention, is performed as a solid phase peptide synthesis. Even more preferably this synthesis is carried out with the Fmoc scheme, wherein Pg is Fmoc.

In another aspect, a process of converting the compound of formula II into degarelix or a pharmaceutically acceptable salt thereof is provided, characterized as comprising the steps of:

a) treating the compound of formula II with a reducing agent to form a compound of formula III, Formula III

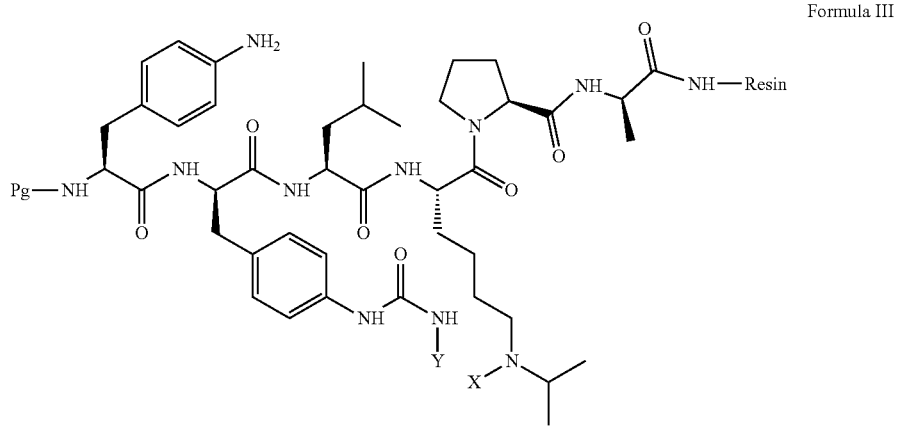

b) reacting the compound of formula III with an activated dihydroorotic acid, to form a compound of formula IV, Formula IV

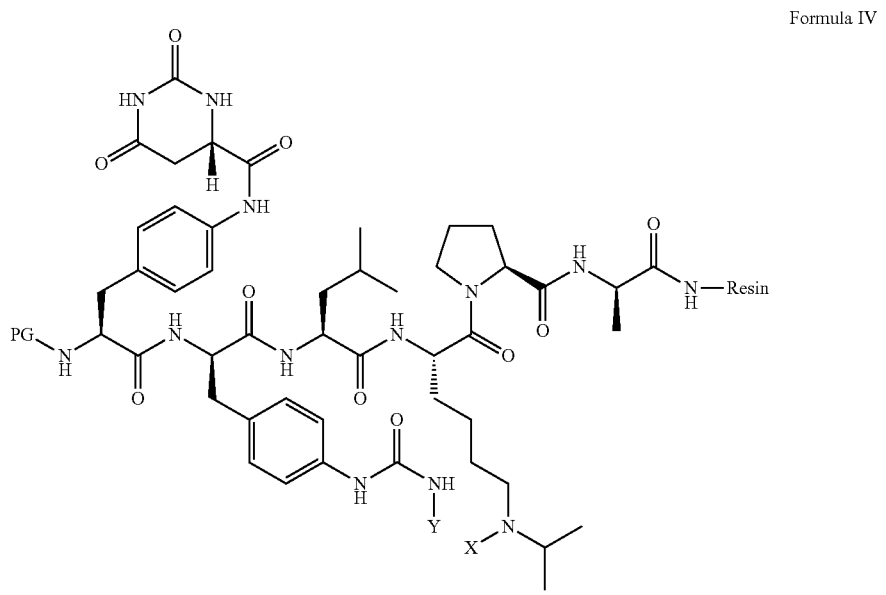

c) repeating the following steps (i)-(ii) until formation of a protected decapeptide, preferably attached to a resin by solid phase peptide synthesis:
  (i) deprotecting the protected peptide attached to the resin to remove terminal protecting group,
  (ii) coupling of the protected amino acid (according to required sequence) to the terminal amino group residue attached to the resin using a coupling reagent to form a protected peptide attached to the resin,
d) deprotecting the protected decapeptide attached to resin to remove the terminal protecting group,
e) acetylating the N-terminus of the resulting decapeptide in the presence of an acetylating agent, and
f) cleaving the acetylated decapeptide from the resin to form degarelix or a pharmaceutically acceptable salt thereof wherein Pg is a terminal protecting group, X is a side chain protecting group and Y is a side chain protecting group or H, and Resin is a solid support.

In another aspect, a process of converting the compound of formula II into degarelix or a pharmaceutically acceptable salt thereof, preferably as a solid phase peptide synthesis, is provided characterized as comprising the steps of:
  a) providing the compound of formula II,
  b) repeating the following steps (i)-(ii) until the formation of a protected decapeptide attached to the resin:
    (i) deprotecting the protected peptide attached to the resin to remove the terminal protecting group,
    (ii) coupling of the protected amino acid (according to required sequence) to the terminal amino group residue attached to the resin using a coupling reagent to form a protected peptide attached to the resin,
  c) deprotecting the protected decapeptide attached to the resin to remove terminal protecting group,
  d) acetylating the N-terminus of resulting decapeptide in the presence of acetylating agent to give a compound of formula V, Formula V

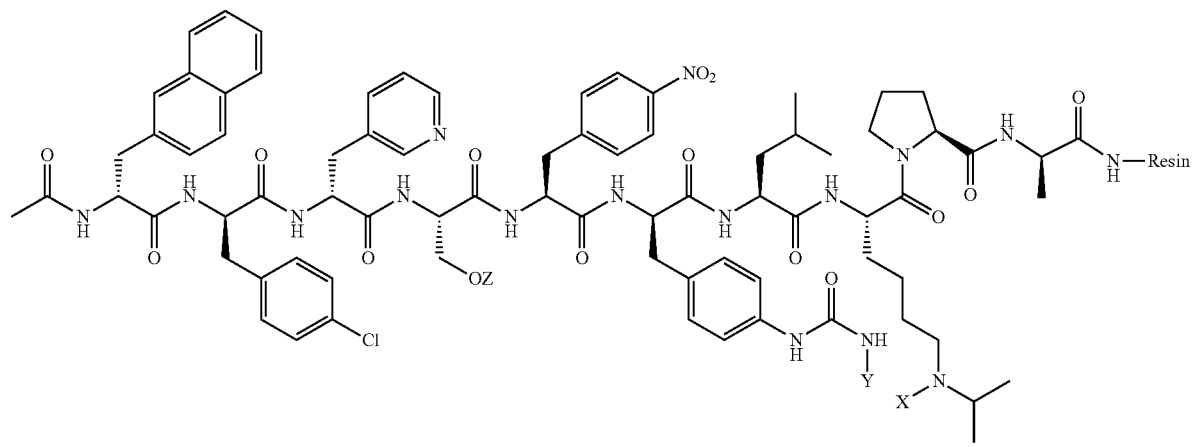

e) treating the compound of formula V with a reducing agent to form a compound of formula VI, Formula VI

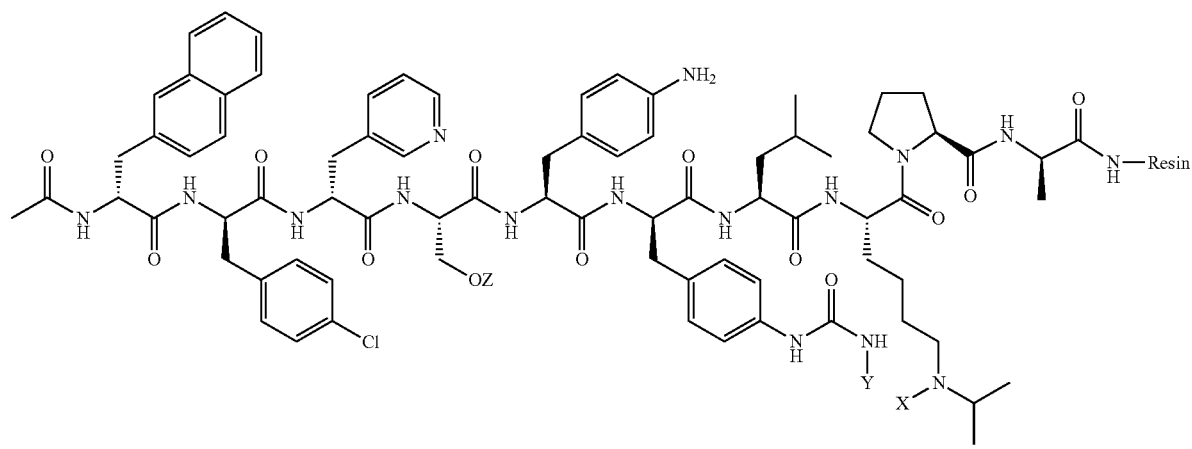

f) reacting the compound of formula VI with an activated dihydroorotic acid, to form a protected decapeptide attached to the resin; and g) cleaving the decapeptide from the resin to form degarelix or a pharmaceutically acceptable salt thereof
wherein X, and Z are side chain protecting groups, and Y is a side chain protecting group or H, and "Resin" is a solid support.

As another aspect a process for the solid phase synthesis of the compound of formula II, is provided, comprising the steps of:

a) reducing a compound of formula VII,

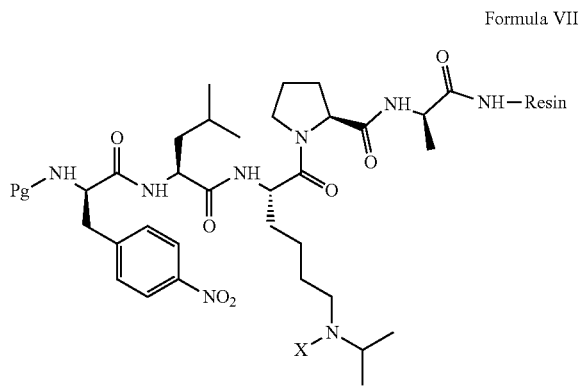

Formula VII wherein Pg is a terminal protecting group, X is a side chain protecting group, and "Resin" is a solid support with a reducing agent to form a compound of formula VIII,

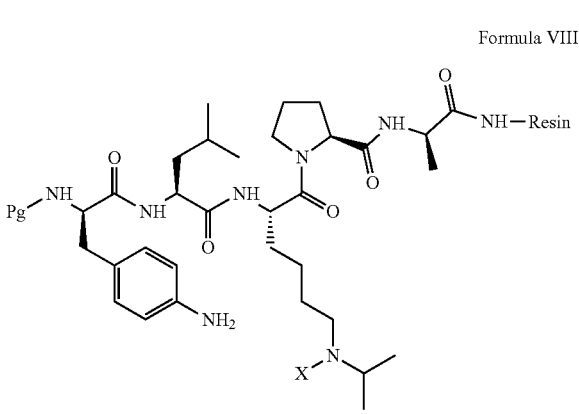

Formula VIII wherein Pg is a terminal protecting group; X is a side chain protecting group and "Resin" is a solid support b) reacting the compound of formula VIII with alkyl isocyanate or alkali metal cyanate to form a compound of formula IX,

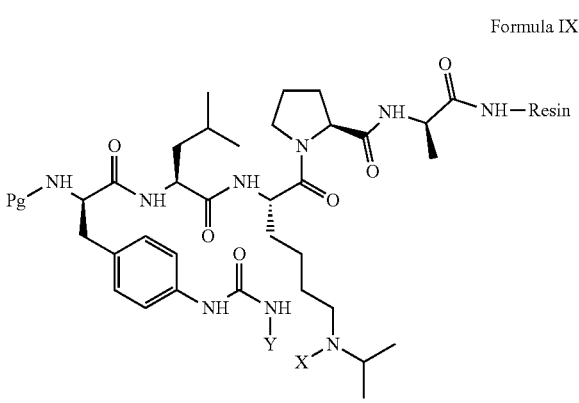

Formula IX wherein Pg is a terminal protecting group, X and Y are side chain protecting groups or, Y is H if an alkali metal cyanate is used, and resin is a solid support, and c) deprotecting the compound of formula IX to remove the terminal protecting group followed by coupling with the protected amino acid of formula X,

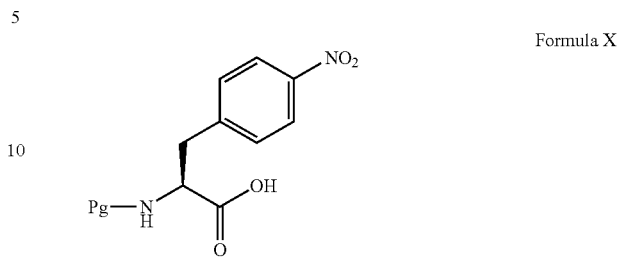

Formula X wherein Pg is a terminal protecting group in the presence of a coupling reagent to form the compound of formula II.

As another aspect a process for the solid phase synthesis of the compound of formula VII, is provided, comprising the step of deprotecting the compound of formula XI,

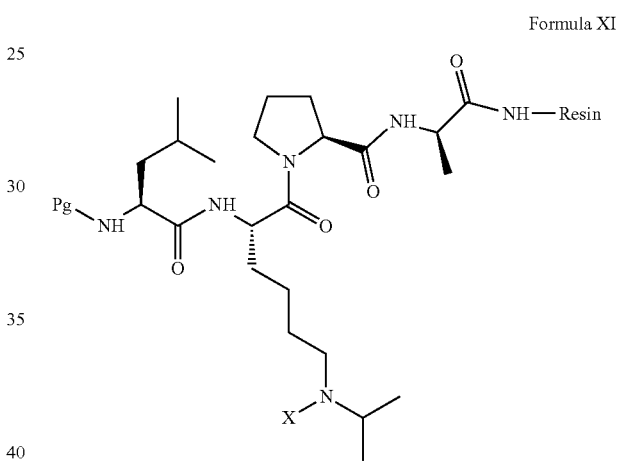

Formula XI wherein Pg is a terminal protecting group, X is a side chain protecting group, and resin is a solid support, to remove the terminal protecting group followed by coupling with protected amino acid of formula X (D-isomer) in the presence of a coupling reagent to form the compound of formula VII.

Another aspect of the present invention is to provide the compounds of formula II, formula V and formula VII.

Still another aspect of the present invention is the use of these compounds in the synthesis of degarelix.

DETAILED DESCRIPTION OF THE INVENTION

Figure 1:
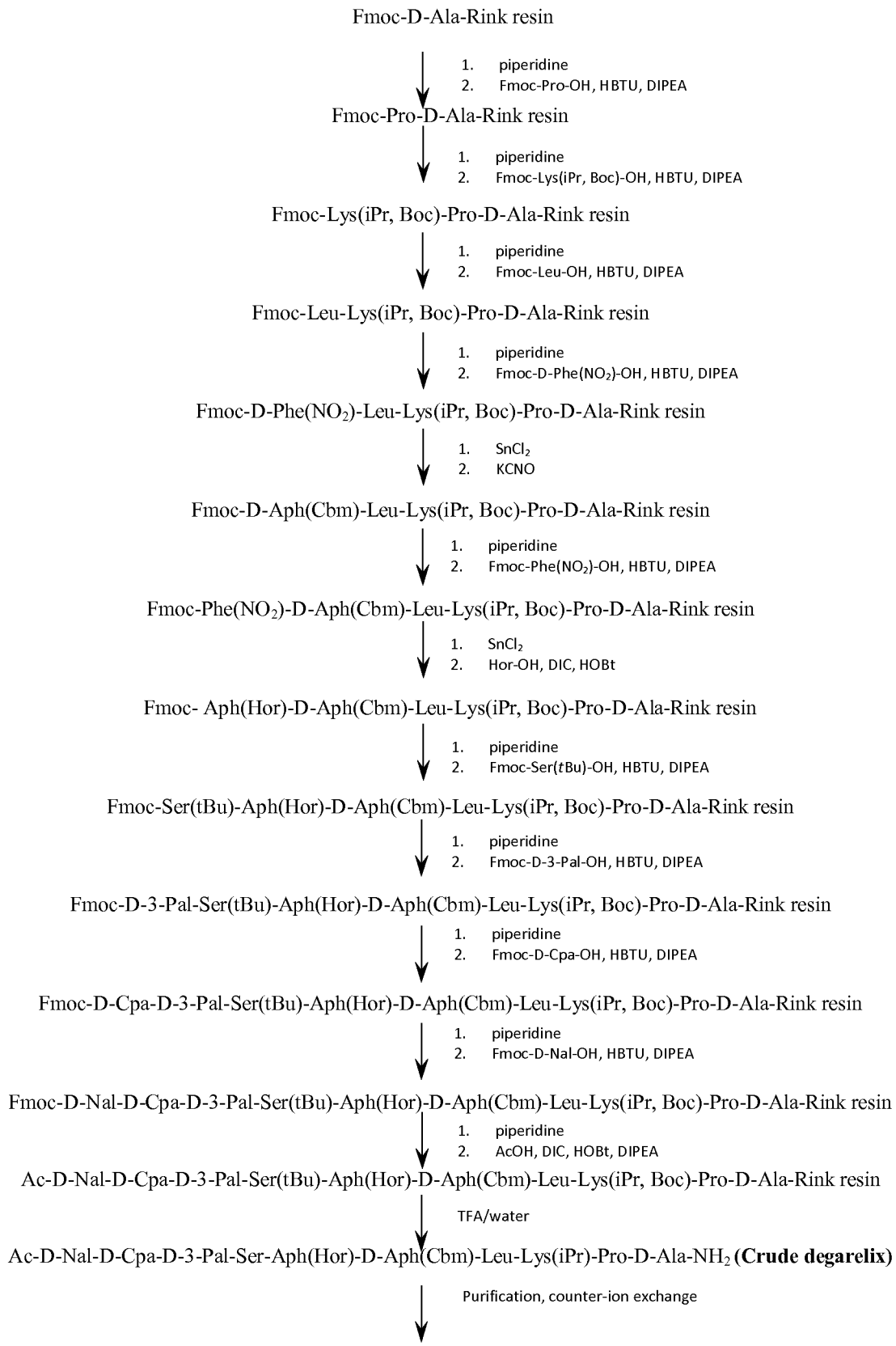
FIG. 1: This figure shows a scheme of the solid phase synthesis of degarelix acetate using a suitable peptide precursor thereby incorporating L-p-nitro-Phe and D-p-nitro-Phe residues at the $5^{th}$ and $6^{th}$ position, respectively.

The term "terminal protecting group" as used herein refers to a protecting group of the carbamate type. The preferred terminal protecting group is Fmoc (9-fluorenylmethyloxycarbonyl), which can be removed in acidic conditions. In another embodiment the terminal protecting group is BOC.

As used herein, the term "side-chain protecting group" is referring to a protecting group for an amino- or hydroxyl group, in a side chain of the peptide, which is removed under suitable conditions, it is not removed under those conditions when the terminal protecting group or another amino-protecting group is removed. Preferably side chain protecting groups are included to protect side chains of amino acids which are particularly reactive or labile, to avoid side reactions and/or branching of the growing molecule. The criterion for selecting a suitable side chain protecting group X, Y and Z is that the protecting group should generally be stable to the reagent under the reaction conditions selected for removing the terminal amino protecting group at each step of the synthesis and should be removable upon completion of the synthesis of the desired amino acid sequence under reaction conditions that will not alter the peptide chain. Preferably X is an amine protecting group such as tertbutyloxycarbonyl(Boc); Y is a hydrogen or an amine protecting group such as an alkyl or more preferably a tert-butyl group; Z is a hydroxyl protecting group such as tert-butyl.

As used herein the term "salt" includes acid salts, such as for example, hydrochlorides, and acetates.

As used herein the term "peptide" is understood to be a sequence of amino acids, or amino acid derivatives, coupled one to another by peptide bonds, of a minimum length of 2 amino acids. The term "nitro-peptide" as used herein is such a peptide comprising one or two p-nitro-phenylalanine residues.

The term decapeptide is comprised of a chain of ten amino acids coupled by peptide bonds.

Throughout the description wherein the term "Resin" is used it is understood to comprise a solid support suitable to perform solid phase peptide synthesis, which allows obtaining a C-terminal amide after cleavage from the resin, unless "Resin" is explicitly declared to be H (proton). In that case the free (unbound) form of the peptide is comprised in the reference. A preferred solid support for a Fmoc based synthesis is one selected from the group consisting of the Rink Amide resin, Rink amide AM resin and Rink amide MBHA resin; more preferably the resin is the Rink amide MBHA resin. A preferred solid support for a Boc based synthesis is Benzhydrylamine resin (BHA) or 4-Methylbenzhydrylamine resin (MBHA), more preferably Methylbenzhydrylamine resin.

As used herein the term "activated acid" means an acid derivative that is able to form a peptide bond after the reaction with an amine.

The term "activated dihydroorotic acid" is understood to be dihydroorotic acid activated by the presence of one or more coupling reagents, or to be a derivative of dihydroorotic acid, such as HOR—CO—Hal, where Hal is Cl, Br or F.

The present invention provides an improved process for the preparation of a peptide, preferably a peptide, characterized as having at least one Aph derivative in its sequence, preferably an Aph(Hor) or Aph(Cbm), more preferably a decapeptide or a pharmaceutically acceptable salt thereof by incorporation of p-nitrophenylalanine residues in those positions which are Aph derivatives, preferably Aph(Hor) and/or Aph(Cbm), in the final peptide. Preferably the peptide is a decapeptide with Aph(Hor) in the $5^{th}$ and Aph(Cbm) in the 6th position. Most preferably the decapeptide is degarelix.

The nitro groups of these p-nitrophenylalanine residues are subsequently reduced to amino groups and these are subsequently modified to obtain Aph(Hor) and D-Aph(Cbm), preferably in position 5 and 6 of the decapeptide, respectively. The modification of these does take place sequentially (not simultaneously).

The inventors have found that surprisingly pharmaceutically pure degarelix can be manufactured by introduction of p-nitrophenylalanine instead of their bulkier derivatives, which are then transferred into the correct amino acid derivatives, Aph(Hor) and D-Aph(Cbm) group, while being incorporated in the peptide, preferably while being bound to a solid phase (i.e. the resin) during SPPS. They also found that this strategy noticeably facilitates or simplifies peptide chain formation. Unexpectedly, this degarelix synthesis characterized by the use of corresponding p-nitro precursors, yields the crude product with a high purity and a beneficial impurity profile, in comparison to the classical approach, disclosed in WO2010/121835, facilitating a much better separation during HPLC purification and thus increasing the final yield.

In a first aspect, a peptide synthesis for preparing degarelix or a pharmaceutically acceptable salt thereof is provided. The improved peptide synthesis of degarelix or a pharmaceutically acceptable salt thereof, is based on the strategy of incorporating into the sequence the p-nitro phenylalanine residues at the $5^{th}$ position in the amino acid sequence used to synthesize degarelix, with subsequent reduction of the nitro groups to amino groups and their modification to obtain Aph(Hor) before further continuing with the synthesis. In a preferred embodiment the synthesis is a solid-phase peptide synthesis. A preferred synthetic approach comprises converting the compound of formula II into degarelix or a pharmaceutically acceptable salt thereof.

The new compound of formula II can be converted to degarelix or a pharmaceutically acceptable salt thereof by different procedures. Two of these are described herein. In one embodiment of the invention, the peptide synthesis of degarelix or a pharmaceutically acceptable salt thereof, involving the compound of formula II, is based on the strategy of subsequent reduction of the incorporated nitro group to an amino group and its modification to obtain Aph(Hor) before further continuing with the solid phase synthesis.

The process comprises the steps of:
a) treating the compound of formula II with a reducing agent to form the compound of formula III,
b) reacting the compound of formula III with an activated dihydroorotic acid, which may be dihydroorotic acid activated by the presence of coupling reagent, to form the compound of formula IV,
c) repeating the following steps (i)-(ii) with different amino acids until the protected decapeptide, which is attached to a resin, is formed:
  (i) deprotecting the protected peptide attached to the resin to remove the terminal protecting group,
  (ii) coupling of the protected amino acid (according to required sequence) to the terminal amino group residue attached to the resin using a coupling reagent to form the protected peptide attached to the resin,
d) deprotecting the protected decapeptide attached to resin to remove the terminal protecting group,
e) acetylating the N-terminus of the resulting decapeptide in the presence of acetylating agent; and
f) cleaving the acetylated decapeptide from the resin to achieve a decapeptide with an Aph(Hor) amino acid at position 5, or a pharmaceutically acceptable salt thereof. Preferably this decapeptide is degarelix.

The reducing agent used in step a) is selected from, but not limited to, sodium dithionite, tin (II) chloride or iron powder. Preferably, the reduction is carried out in the presence of tin (II) chloride.

In step b) the compound of formula III is reacted with an activated dihydroorotic acid to form the compound of formula IV. When, the activation is facilitated by the presence of a coupling reagent, suitable coupling reagents are N,N'-diisopropylcarbodiimide, dicyclohexyl-carbodiimide, ethyl-dimethylaminopropyl carbodiimide (EDC). Preferably, the reaction is carried out in the presence of N,N'-diisopropyl-carbodiimide.

The reaction may also be carried out in the presence of a coupling reagent and an additive. The addition of an additive has been found to reduce racemisation during the formation of amide linkage (i.e. peptide bond formation). An additive, when added to the coupling reaction results in an increased yield and reduced racemisation rates of the peptides formed. Additives form activated esters with amino acids. They suppress the side-reaction, such as formation of oxazolone and N-acylurea. A suitable additive is preferably selected from the group comprising of 1-hydroxybenzotriazole (HOBt), 2-hydroxypyridine N-oxide, N-hydroxysuccinimide, 1-hydroxy-7-azabenzotriazole and endo-N-hydroxy-5-norbornene-2,3-dicarboxamide. More preferably, the reaction is carried out in the presence of N,N'-diisopropylcarbodiimide and 1-hydroxybenzotriazole.

In step c), the protected decapeptide, which is still attached to the resin is prepared by extension of the peptide chain, the concept is known as solid phase peptide synthesis, which involves first removing the terminal protecting group from the protected peptide attached to the resin and then coupling with terminally protected amino acids stepwise in the desired order until the desired decapeptide is formed.

In a first step (i), the N-terminal protecting group—if it is Fmoc—can be removed by treatment with a base, preferably an organic base, more preferably an amine. The base may be selected from the group consisting of piperidine, piperazine, DBU and diethylamine, preferably piperidine and DBU, and most preferably, piperidine are used.

In a second step (ii), coupling of the protected peptide bound to the resin with the next protected amino acid is carried out in the presence of a coupling reagent selected from the group comprising of 1-ethyl-3-(3-dimethylamino-propyl)carbodiimide (EDC), N,N'-dicyclohexylcarbodiimide (DCC), N,N'-diisopropylcarbodiimide, 2-(1H-benzotri-azol-1-yl)-1,1,3,3-tetramethyluronium hexafluorophosphate (HBTU), or any coupling reagents on the base of uronium or phosphonium salts. Preferably, the reaction is carried out in the presence of 2-(1H-benzotriazol-1-yl)-1,1,3,3-tetram-ethyluronium hexafluorophosphate.

The coupling reaction may be carried out in the presence of a base selected from the group comprising of tertiary amine like diisopropylethylamine, triethylamine, N-methyl-morpholine, N-methylpiperidine, preferably, the reaction is carried out in the presence of diisopropylethylamine.

These steps, (i) and (ii), may be repeated until the formation of the desired decapeptide.

To achieve the desired sequence of amino acids resulting in degarelix in the second step, the following terminally protected amino acids need to be coupled in a sequential order: Pg-Ser-OH, Pg-3-Pal-OH, Pg-D-Cpa-OH and Pg-D-Nal-OH in stepwise manner. The amino acid residue can be protected with a side chain protecting group, if required. Preferably Pg-Ser(Z)-OH is used in this peptide synthesis, wherein Z is a side chain protecting group, preferably a t-butyl protecting group.

In step d), after the desired amino acid sequence has been completed, the terminal protecting group is removed by treatment with a base, preferably selected from the group consisting of piperidine, triethylamine, DBU, N-methylmor-pholine and N-methylpiperidine, most preferably with piperidine.

In step e), after deblocking the terminal amino group and while desired side chain groups remain protected, acetylation is carried out. Preferably, this reaction can be carried out with acetic acid, in the presence of diisopropyl or dicyclohexyl carbodiimide (DIC or DCC), or by some other suitable acylation reaction, for example with acetyl imidazole. Alternatively, acetylation is carried out by reacting the peptide with acetic anhydride.

In step f), the acetylated decapeptide is decoupled from the resin by treating the coupled decapeptide with an acid, preferably with trifluoroacetic acid, which not only cleaves the peptide from the resin, but also cleaves all remaining side chain protecting groups to give degarelix acetate.

A preferred method for the synthesis of degarelix using the above described synthesis based on the use of a compound of formula II is described in FIG. 1. FIG. 1 also illustrates one way to achieve a compound of formula II, involving the use of a compound of formula VII.

Another synthetic approach describing the conversion process of a compound of formula II into degarelix or a pharmaceutically acceptable salt thereof, —which is based on incorporation of the p-nitro phenylalanine residues at the $5^{th}$ position in the decapeptide sequence—is characterized by continuing with a solid phase synthesis thereby adding all the amino acids required for the decapeptide, preferably for degarelix. Only after completion of the peptide synthesis, the nitro group of the amino acid residue at the $5^{th}$ position is reduced to an amino group and further modified to Aph(Hor).

The process comprises the steps of:
a) providing the compound of formula II,
b) repeating the following steps (i)-(ii) until a protected decapeptide attached to the resin is formed:
   (i) deprotecting the protected peptide attached to the resin to remove the terminal protecting group, (
   ii) coupling of another amino acid (according to the required sequence), which is protected at the N-terminus to the terminal amino group residue attached to the resin using a coupling reagent to form protected peptide attached to the resin, that is extended by one amino acid;
c) deprotecting the protected decapeptide attached to resin to remove the terminal protecting group,
d) acetylating the N-terminus of the resulting decapeptide in the presence of an acetylating agent to give the compound of formula V,
e) treating the compound of formula V with a reducing agent to form the compound of formula VI,
f) reacting the compound of formula VI with dihydroorotic acid in the presence of a coupling reagent to form the protected decapeptide attached to the resin; and
g) cleaving the decapeptide from the resin to form degarelix or a pharmaceutically acceptable salt thereof.

In step b), the compound of formula II is converted to a protected decapeptide attached to the resin by usual solid phase peptide synthesis, which involves first removing the terminal protecting group and then coupling with terminally protected amino acids stepwise in the desired order until the decapeptide is formed.

In a first step (i), the N-terminal protecting group—if it is Fmoc—can be removed by treatment with a base, preferably an organic base, more preferably an amine. The base may be selected from the group consisting of piperidine, piperazine, DBU and diethylamine, preferably piperidine and DBU, and most preferably, piperidine are used.

In a second step (ii), coupling of the protected peptide bound to the resin with the next protected amino acid is carried out in the presence of a coupling reagent selected from the group comprising of 1-ethyl-3-(3-dimethylaminopropyl)carbodiimide (EDC), N,N'-dicyclohexylcarbodiimide (DCC), N,N'-diisopropylcarbodiimide, 2-(1H-benzotriazol-1-yl)-1,1,3,3-tetramethyluronium hexafluorophosphate (HBTU), or any coupling reagents on the base of uronium or phosphonium salts. Preferably, the reaction is carried out in the presence of 2-(1H-benzotriazol-1-yl)-1,1,3,3-tetramethyluronium hexafluorophosphate.

The coupling reaction may be carried out in the presence of a base selected from the group comprising of tertiary amine like diisopropylethylamine, triethylamine, N-methylmorpho line, N-methylpiperidine, preferably, the reaction is carried out in the presence of diisopropylethylamine.

The first and the second step (i) and (ii) may be repeated until the desired decapeptide is formed.

To produce degarelix as the preferred decapeptide, described in the second step the following terminally protected amino acids have to be coupled sequentially in stepwise manner: Pg-Ser-OH, Pg-3-Pal-OH, Pg-D-Cpa-OH and Pg-D-Nal-OH. The amino acid residue can be protected with a side chain protecting group, if required. Preferably Pg-Ser(Z)—OH is used for the peptide synthesis, wherein Z is side chain protecting group. Preferably Z is a hydroxy protecting group such as, for example, tBu or trityl group.

After the desired amino acid sequence has been completed, in step c) the terminal protecting group is removed by treatment with a suitable base, according to the conditions as described above, preferably selected from the group consisting of piperidine, triethylamine, DBU, N-methylmorpholine and N-methylpiperidine, most preferably piperidine.

In step d), after deblocking the terminal amino group and while desired side chain groups remain protected, acetylation is preferably carried out. Preferably, the resin bound peptide is treated with acetic acid, in the presence of diisopropyl or dicyclohexyl carbodiimide (DIC or DCC). Alternatively the reaction can be carried out with acetic anhydride, or by some other suitable acylation reaction, for example with acetyl imidazole. The acetylation process results in the compound of formula V.

In step e) the compound of formula V is reduced to compound of formula VI. The reducing agent used is selected from, but not limited to, sodium dithionite or tin (II) chloride. Preferably, the reduction is carried out in the presence of tin (II) chloride.

In step f) the compound of formula VI is reacted with activated dihydroorotic acid, to form a protected decapeptide attached to the resin. If the activation is based on the presence of a coupling agent, the coupling reagent may be selected from the group comprising N,N'-diisopropylcarbodiimide, dicyclohexylcarbodiimide and ethyl-dimethyl-aminopropyl carbodiimide (EDC). Preferably, the reaction is carried out in the presence N,N'-diisopropylcarbodiimide.

The reaction may also be carried out in the presence of a coupling reagent and an additive. The addition of an additive has been found to reduce racemisation during the formation of amide linkage (i.e. peptide bond formation). An additive, when added to the coupling reaction results in an increased yield and reduced racemisation rates of the peptides formed. Additives form activated esters with amino acids. They suppress the side-reaction, such as formation of oxazolone and N-acylurea. A suitable additive is preferably selected from the group comprising of 1-hydroxybenzotriazo le (HOBt), 2-hydroxypyridine N-oxide, N-hydroxysuccinimide, 1-hydroxy-7-azabenzotriazole and endo-N-hydroxy-5-norbornene-2,3-dicarboxamide. More preferably, the reaction is carried out in the presence of N,N'-diisopropylcarbodiimide and 1-hydroxybenzotriazole.

In step g), the desired peptide is decoupled from the resin by treating the resin bound peptide with an acid, preferably trifluoroacetic acid, which not only cleaves the peptide from the resin, but also cleaves all remaining side chain protecting groups.

Figure 2:
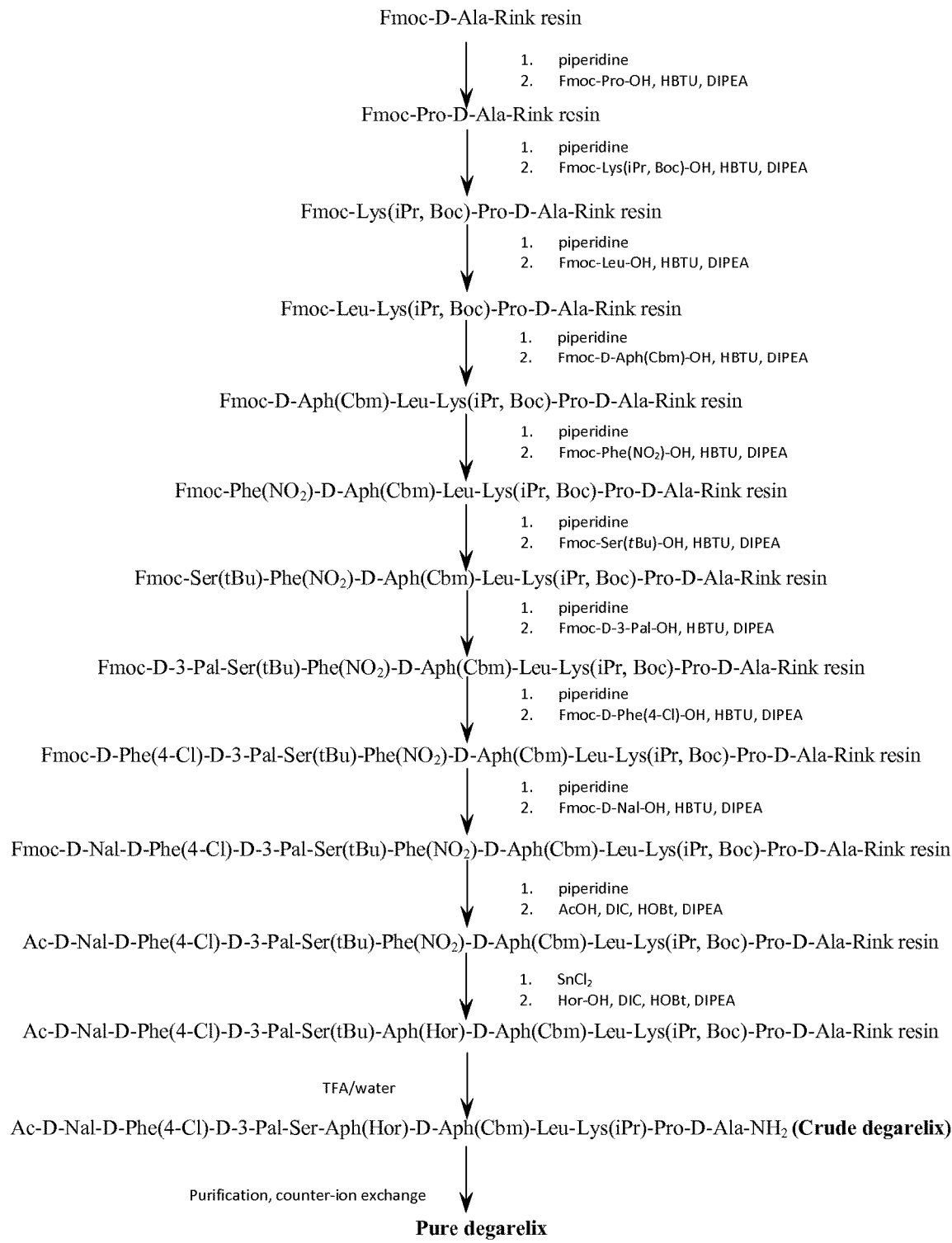
FIG. 2: This figure shows a scheme of the solid phase synthesis of degarelix acetate by using a suitable peptide precursor thereby incorporating L-p-nitro-Phe residue at $5^{th}$ position.

A preferred method for the synthesis of degarelix using the above described synthesis, based on the use of a compound of formula II is illustrated in FIG. 2. FIG. 2 also illustrates an alternative way to synthesize the compound of formula II.

Degarelix prepared by the process(es) of the present invention is characterized by an impurity profile which allows for a more effective purification via the standard purification method, HPLC purification. Moreover, it allows preparing degarelix without previous synthesis of Aph derivatives, thereby significantly simplifying the synthetic approach and allowing for a more economic process.

The compound of formula II as used in the processes described above can be prepared by the novel processes described below.

In another aspect, a process for the solid phase synthesis of the compound of formula II is provided, comprising the steps of:

a) reducing the compound of formula VII with a reducing agent to form the compound of formula VIII, b) reacting the compound of formula VIII with alkyl isocyanate or alkali metal cyanate to form the compound of formula IX, and c) deprotecting the compound of formula IX to remove the terminal protecting group followed by coupling with a protected amino acid of formula X in the presence of a coupling reagent to form the compound of formula II In step a) the compound of formula VII is reduced to a compound of formula VIII. The reducing agent used is selected from, but not limited to, sodium dithionite or tin (II) chloride. Preferably, the reduction is carried out in the presence of tin (II) chloride.

In step b), the reaction of the compound of formula VIII with alkali metal cyanate, preferably with potassium cyanate or sodium cyanate results in the compound of formula IX, wherein the side chain protecting group Y is hydrogen. In another alternative way, the reaction of the compound of formula VIII with alkyl isocyanate, such as tert-butyl isocyanate or trityl isocyanate results in the compound of formula IX, wherein the side chain protecting group Y is alkyl. The reaction may be carried out in the solvents selected from the group comprising of polar aprotic solvents like dimethylformamide, or N-methylpirrolidone. Preferably, the reaction is carried out in dimethylformamide.

In step c), the N-terminal protecting group—if it is Fmoc—can be removed by treatment with a base, preferably an organic base, more preferably an amine. The base may be selected from the group consisting of piperidine, piperazine, DBU and diethylamine, preferably piperidine and DBU, and most preferably, piperidine are used. After removal of the protecting group, the compound of the resulting peptide is coupled with a compound of formula X (L isomer) in the presence of a coupling agent to give the compound of formula II. The coupling reagent can be selected from the group comprising of 1-ethyl-3-(3-dimethylaminopropyl)carbodiimide (EDC), N,N'-dicyclohexylcarbodiimide (DCC), N,N'-diisopropylcarbodiimide, 2-(1H-benzotriazol-1-yl)-1, 1,3,3-tetramethyluronium hexafluorophosphate (HBTU) or any coupling reagents on the basis of uronium or phosphonium salts. Preferably, the reaction is carried out in the presence of 2-(1H-benzotriazol-1-yl)-1,1,3,3-tetramethyluronium hexafluorophosphate.

In another aspect, the compounds of formula II, V and VII are provided as novel intermediates for the synthesis of decapepeptides, preferably for the synthesis of degarelix. These intermediate peptides are disclosed herewith in their free form (where Resin is H), as well as in their form bound to a solid support (where Resin is a solid support).

The compound of formula VII, which is employed in a process to prepare a compound of formula II is novel and can be prepared as described below.

In still another aspect, a process for the synthesis of the compound of formula VII is provided characterized as comprising the steps of deprotecting the compound of formula XI to remove the terminal protecting group followed by coupling with a protected amino acid of formula X (D-isomer) in the presence of a coupling reagent to form the compound of formula VII.

The terminal protecting group can be removed by treatment with a base, preferably an organic base, more preferably an amine. The base may be selected from the group consisting of piperidine, piperazine, DBU and diethylamine, preferably piperidine and DBU, and most preferably, piperidine are used. After the removal of the protecting group, the resulting peptide is coupled with the D-isomer of the compound of formula X. The coupling is performed in the presence of a coupling agent and results in the formation of the compound of formula VII. The coupling reagent can be selected from the group comprising of 1-ethyl-3-(3-dimethylaminopropyl)carbodiimide (EDC), N,N'-dicyclohexylcarbodiimide (DCC), N,N'-diisopropylcarbodiimide, 2-(1H-benzotriazol-1-yl)-1,1,3,3-tetramethyluronium hexafluorophosphate (HBTU) or any coupling reagents on the base of uronium or phosphonium salts. Preferably, the reaction is carried out in the presence of 2-(1H-benzotriazol-1-yl)-1,1,3,3-tetramethyluronium hexafluorophosphate.

The solid phase synthesis as described above may be carried out in aprotic solvents selected from the group comprising dimethylformamide, and N-methylpyrrolidone. Preferably, the reaction is carried out in dimethylformamide.

A preferred method for releasing degarelix from the solid support is by acidic treatment, more preferably, by treatment with TFA.

By using the synthetic approaches described above the incorporation of the entire residues Aph(Hor) and D-Aph (Cbm), or at least the incorporation of Aph(Hor) can be avoided. Thereby the complications accompanying the insertion of such a bulky amino acid residue can be eliminated, and the formation of corresponding des-peptides (deletion peptides, which lack one or more amino acids) is strongly decreased. Therefore, the construction of Aph (Hor)- or Aph (Hor)- and D-Aph(Cbm)-group in the peptide can noticeably enhance the purity of the obtained crude peptide, in particular when performed as solid state peptide synthesis. The impurity profile that can be achieved with this new synthesis is favorable for the routine follow-up purification with HPLC because the impurities are easier to separate. Moreover, the method can noticeably facilitate the overall synthesis of the peptide, since in this case there is no need to prepare and purify the intermediate Aph derivatives to be inserted into peptide sequence. All the side products and excess of the reagents during the construction of these residues can be easily removed by filtration and washing.

Thus, the synthetic approaches described above employ less bulky intermediates, by using the compounds of Formula II and/or X, avoid the use of hazardous reagents and provide a simple process for the synthesis of degarelix or salts thereof, which results in a product with higher yield and/or higher purity than the methods known in the art.

Preferred Embodiments of the Invention

1. A method for preparing a peptide, wherein the peptide is characterized as being a peptide with at least one Aph derivative, preferably selected from Aph(Hor) and Aph (Cbm), in the peptide sequence or a pharmaceutically acceptable salt thereof, wherein the method comprises the use of either p-nitrophenylalanine or a nitro-peptide, preferably resulting in incorporation of at least one or preferably one nitrophenylalanine into the peptide sequence; followed by modification of incorporated nitrophenylalanine residues within the peptide sequence into the respective Aph derivative. Preferably the peptide is a decapeptide. More preferably Aph(Hor) and/or Aph(Cbm) are in the $5^{th}$ and $6^{th}$ position.

2. A method according to embodiment 1 wherein the peptide is degarelix of formula I, or a pharmaceutically acceptable salt thereof.

3. A method according to embodiment 1 or 2 wherein said nitro-peptide is characterized as comprising one or two p-nitrophenylalanine residues, and preferably wherein said nitro-peptide is a compound of formula II,V or VII, most preferably of formula II 4. A method according to any of the embodiments above, wherein the method comprises converting a compound of formula II, wherein Pg is a terminal protecting group, X and Y are side chain protecting groups, and Resin is H or a solid support, into degarelix or a pharmaceutically acceptable salt thereof.

5. A method according to any of the embodiments above, wherein the method is performed as solid phase peptide synthesis.

6. The method according to any of the embodiments above, characterized as comprising the steps of:
  a) treating the compound formula II with a reducing agent to form a compound of formula III, wherein Pg is a terminal protecting group, X and Y are side chain protecting groups, and Resin is a solid support
  b) reacting the compound of formula III with an activated dihydroorotic acid to form a compound formula IV, wherein Pg is a terminal protecting group, X and Y are side chain protecting groups, and Resin is a solid support
  c) repeating the following steps (i)-(ii) attached to resin until a protected decapeptide is formed:
    (i) deprotecting the protected peptide to remove the terminal protecting group,
    (ii) coupling of the protected amino acid (according to required sequence) to the terminal amino group residue of the peptide attached to the resin using a coupling reagent to form a by one amino acid elongated protected peptide,
  d) deprotecting the protected decapeptide to remove the terminal protecting group,
  e) acetylating the N-terminus of the resulting decapeptide in the presence of an acetylating agent, and
  f) cleaving the acetylated decapeptide peptide from the resin to form degarelix or a pharmaceutically acceptable salt thereof;
  thereby converting a compound of formula II in degarelix or a pharmaceutically acceptable salt thereof.

7. The method according to embodiment 6, wherein in step b) the activated dihydroorotic acid is activated by a coupling reagent, which is selected from a group comprising N,N'-diisopropylcarbodiimide, dicyclohexylcarbodiimide and ethyl-dimethyl-aminopropyl carbodiimide (EDC), preferably said coupling reagent is N,N'-diisopropylcarbodiimide, preferably N,N'-diisopropylcarbodiimide in combination with 1-hydroxybenzotriazo le.

8. The method according to any of embodiments 1 to 5, comprising the steps of:
  a) providing the compound of formula II,
  b) repeating the following steps (i)-(ii) until a protected decapeptide attached to resin is formed:
    (i) deprotecting the protected peptide attached to the resin to remove the terminal protecting group,
    (ii) coupling of the protected amino acid according to required sequence to the terminal amino group residue attached to the resin using a coupling reagent to form protected peptide attached to the resin;

c) deprotecting the protected decapeptide to remove terminal protecting group,
d) acetylating the N-terminus of the resulting decapeptide in the presence of an acetylating agent to result in a compound of formula V, wherein X, Y and Z are side chain protecting groups, and Resin is a solid support;
e) treating the compound of formula V with a reducing agent to form a compound of formula VI, wherein X, Y and Z are side chain protecting groups, and Resin is a solid support;
f) reacting the compound of formula VI with activated dihydroorotic acid to form a protected decapeptide attached to the resin; and
g) cleaving the decapeptide from the resin to form degarelix or a pharmaceutically acceptable salt thereof.

9. The method according to embodiment 8, wherein in step e) the reducing agent is selected from sodium dithionite or tin (II) chloride, preferably tin (II) chloride.

10. The method according to embodiment 8, wherein in step f) the activated dihydroorotic acid is activated by a coupling reagent, which is selected from the group comprising N,N'-diisopropylcarbodiimide, dicyclohexylcarbodiimide and ethyl-dimethyl-aminopropyl carbodiimide (EDC), preferably said coupling reagent is N,N'-diisopropylcarbodiimide, more preferably N,N'-diisopropylcarbodiimide in combination with 1-hydroxybenzotriazole.

11. The compound of formula II, wherein Pg is a terminal protecting group or H, X and Y are side chain protecting groups or H, and Resin is a solid support or, and wherein the compound is not attached to a solid support, the Resin is H.

12. A method for preparing the compound of formula II, characterized as comprising the following steps:
a) reducing a compound of formula VII, wherein Pg is a terminal protecting group; X is a side chain protecting group, and Resin is a solid support with a reducing agent to form a compound of formula VIII, wherein Pg is a terminal protecting group; X is a side chain protecting group, and Resin is a solid support;
b) reacting the compound of formula VIII with alkyl isocyanate or alkali metal cyanate to form a compound of formula IX, wherein Pg is a terminal protecting group, X and Y are side chain protecting groups, wherein Y is H when an alkali metal cyanate is present, and Y is tBu or another alkyl group, when alkyl isocyanate is present and Resin is a solid support;
c) deprotecting the compound of formula IX to remove the terminal protecting group followed by coupling with the protected D-isomer of the amino acid of formula X, wherein Pg is a terminal protecting group, preferably Fmoc, in the presence of a coupling reagent to form the compound of formula II.

13. The process according to embodiment 6 or 12, wherein in step a) the reducing agent is sodium dithionite or tin (II) chloride, preferably tin (II) chloride.

14. The method according to embodiment 12, wherein preparing the compound of formula VII, comprises the step of deprotecting the compound of formula XI, wherein Pg is a terminal protecting group, X is a side chain protecting group and Resin is a solid support; by removing the terminal protecting group; followed by a step of coupling the D isomer of the protected amino acid of formula X in the presence of a coupling reagent to form the compound of formula VII.

15. The process according to embodiment 12, wherein the coupling reagent is selected from the group consisting of 1-ethyl-3-(3-dimethylaminopropyl)carbodiimide (EDC), N,N'-dicyclohexylcarbodiimide (DCC), N,N'-diisopropylcarbodiimide and 2-(1H-benzotriazol-1-yl)-1,1,3,3-tetramethyluronium hexafluorophosphate (HBTU), preferably, 2-(1H-benzotriazol-1-yl)-1,1,3,3-tetramethyluronium hexafluorophosphate (HBTU).

16. A compound of formula V, wherein X, Y and Z are side chain protecting groups, or H and Resin is a solid support and, wherein the compound is not attached to a solid support, the Resin is H.

17. A compound of formula VII, wherein Pg is a terminal protecting group or H, X is a side chain protecting group or H and Resin is a solid support and/or, wherein the peptide is not attached to a solid support the Resin is H.

18. Use of a compound of formula X, formula II, formula V or of formula VII for the synthesis of a peptide, preferably for synthesis of degarelix.

19. A method according to any of the embodiments describing methods of synthetic processes above characterized as being based on the Fmoc protection strategy, wherein the terminal protection group Pg is the base-labile protective group Fmoc.

Abbreviations

| | |
|---|---|
| Aph | Aminophenylalanin |
| Amf | Aminomethylphenylalanine |
| For | Formyl |
| Imz | 2-imidazolidone-4-carbonyl |
| GnRH | Gonadotropin releasing hormone |
| SPPS | Solid phase peptide synthesis |
| LPPS | Liquid phase peptide synthesis |
| MBHA resin | Methyl benzhydryl amide resin |
| Fmoc-Rink amide AM-resin | 4-(2',4'-Dimethoxyphenyl-Fmoc-aminomethyl)-phenoxyacetamidomethyl polystyrene resin |
| Fmoc-Rink amide-MBHA resin | 4-(2',4'-Dimethoxyphenyl-Fmoc-aminomethyl)-phenoxyacetamido-4-methylbenzhydrylamine polystyrene resin |
| Fmoc-D-Ala-Rink resin | 9-Fluorenylmethyloxycarbonyl-D-alanine-Rink resin |
| Fmoc-D-Ala-OH | 9-Fluorenylmethyloxycarbonyl-D-alanine |
| Fmoc-Pro-OH | 9-Fluorenylmethyloxycarbonyl-L-proline |
| Fmoc-Lys(iPr, Boc)-OH | 9-Fluorenylmethyloxycarbonyl-N($\varepsilon$)-isopropyl-N($\varepsilon$)-Boc-lysine |
| Fmoc-Leu-OH | 9-Fluorenylmethyloxycarbonyl-leucine-OH |
| Fmoc-D-Phe(NO$_2$)-OH | Fluorenylmethoxycarbonyl-D-4-nitrophenylalanine |
| Fmoc-Phe(NO$_2$)-OH | Fluorenylmethoxycarbonyl-4-L-nitrophenylalanine |
| Fmoc-D-Aph(Cbm)-OH | 9-Fluorenylmethyloxycarbonyl-N(4)-carbamoyl-D-4-aminophenylalanine |

| | -continued |
|---|---|
| Fmoc-Ser(tBu)-OH | 9-Fluorenylmethyloxycarbonyl-O-t-butyl-serine |
| Fmoc-D-3-Pal-OH | 9-Fluorenylmethyloxycarbonyl-D-3-pyridylalanine |
| Fmoc-D-Cpa-OH/Fmoc-D-Phe(4-Cl)-OH | 9-Fluorenylmethyloxycarbonyl-D-4-chlorophenylalanine |
| Fmoc-D-Nal-OH | 9-Fluorenylmethyloxycarbonyl-D-2-naphtylalanine |
| Fmoc-Aph(L-Hor)-OH | 9-Fluorenylmethyloxycarbonyl-N(4)-(L-hydroorotyl)-4-aminophenylalanine |
| Aph(Hor) | N(4)-(L-hydroorotyl)-4-aminophenylalanine |
| D-Aph(Cbm) | 4-(Aminocarbonyl)amino-D-Phenylalanine |
| Aph(Trt) | 4-(trityl)amino-D-Phenylalanine |
| Hor | Dihydroorotyl |
| Fmoc | 9-Fluorenylmethyloxycarbonyl |
| Boc | t-Butyloxycarbonyl |
| Dde | 1,1-Dichloro-2,2-bis(p-chlorophenyl)ethylene |
| HPLC | High pressure liquid chromatography |
| L-p-nitro-Phe | L-p-nitrophenylalanine |
| D-p-nitro-Phe | D-p-nitrophenylalanine |
| DIPEA | Diisopropylethylamine |
| tBu-NCO | tert-butyl isocyanate |
| $Ac_2O$ | Acetic anhydride |
| $SnCl_2$ | Tin (II) chloride |
| Hor-OH | Dihydroorotic acid |
| HOBt | 1-Hydroxybenzotriazole. |
| TFA | Trifluoroacetic acid |
| DCC | N,N'-dicyclohexylcarbodiimide |
| EDC | 1-Ethyl-3-(3-dimethylaminopropyl) carbodiimide |
| DIC | Diisopropylcarbodiimide |
| HBTU | 2-(1H-benzotriazol-1-yl)-1,1,3,3-tetramethyluronium hexafluorophosphate |

EXAMPLES

Detailed experimental parameters suitable for the preparation of degarelix according to the present invention are provided by the following examples, which are intended to be illustrative and not limiting of all possible embodiments of the invention.

Example 1

Preparation of Degarelix Via Solid Phase Synthesis

Step 1: Preparation of Fmoc-D-Phe(p-$NO_2$)-Leu-Lys(Boc, iPr)-Pro-D-Ala-Rink Resin Synthesis of the protected peptide was carried out by step-by-step solid phase peptide synthesis using Rink amide resin (200 mg, loading 0.65 mmol/g). After swelling of the resin in 2 ml of dimethylformamide Fmoc protective group was removed by 20% solution of piperidine in dimethylformamide (2×2 ml, 5 min and 20 min) and the resin was washed with dimethylformamide (4×2 ml). Fmoc-D-Ala-OH, Fmoc-Pro-OH, Fmoc-Lys(Boc, iPr)—OH, Fmoc-Leu-OH and Fmoc-D-Phe(p-$NO_2$)—OH (three-fold excess respect to the loading of the resin and two-fold excess in case of Fmoc-Lys(Boc, iPr)—OH) were activated by HBTU (150 mg, 0.4 mmol) in presence of diisopropylethylamine (136 µl, 0.67 mmol) and coupled to the resin in 50 min to get Fmoc-protected pentapeptide. The intermediate Fmoc deprotection was carried out as described above.

Step 2: Preparation of Fmoc-D-Aph-Leu-Lys(Boc, iPr)-Pro-D-Ala-Rink Resin

The obtained peptide resin was treated with a solution of $SnCl_2$ (0.6 g, 3.2 mmol) and diisopropylethylamine (70 µl, 0.4 mmol) in 2.5 ml of dimethylformamide for 15 hours. At the end of the reaction the solvent was filtered off and the resin was washed with dimethylformamide (3×2 ml).

Step 3: Preparation of Fmoc-D-Aph(Cbm)-Leu-Lys(Boc, iPr)-Pro-D-Ala-Rink Resin

A solution of potassium cyanate (60 mg, 0.74 mmol) in 2.5 ml of dimethylformamide, containing 10% of 85% phosphoric acid (v/v) was added to the obtained peptide linked to the resin. The reaction was left to continue for 6 hours, the solvent was filtered off and the freshly prepared solution of potassium cyanate was added. After 6 hours the resin was washed with dimethylformamide (3×2 ml), Fmoc protective group was removed by 20% solution of piperidine in dimethylformamide (2×2 ml, 5 min and 20 min) and the resin was washed again with dimethylformamide (4×2 ml).

Step 4: Preparation of Fmoc-Aph-D-Aph(Cbm)-Leu-Lys(Boc, iPr)-Pro-D-Ala-Rink Resin Fmoc-Phe(p-$NO_2$)-OH (170 mg, 0.4 mmol) was activated with HBTU (150 mg, 0.4 mmol) in presence of diisopropylethylamine (136 µl, 0.67 mmol) and added to the peptide resin. After completion of the coupling reaction the resin was washed with dimethylformamide (3×2 ml) and treated with a solution of $SnCl_2$ (0.6 g, 3.2 mmol) and diisopropylethylamine (70 µl, 0.4 mmol) in 2.5 ml of dimethylformamide for 15 hours. At the end of the reaction the resin was washed with dimethylformamide (3×2 ml).

Step 5: Preparation of Fmoc-Aph(Hor)-D-Aph(Cbm)-Leu-Lys(Boc, iPr)-Pro-D-Ala-Rink Resin A solution of dihydroorotic acid (60 mg, 0.36 mmol), diisopropylcarbodiimide (60 µl, 0.39 mmol), hydroxybenzotriazole (52 mg, 0.39 mmol) and diisopropylethylamine (114 µl, 0.65 mmol) in 2.5 ml of dimethylformamide was added to the resin. After 2 and 4 hours the solvent was filtered off and freshly prepared mixture of dihydroorotic acid, N,N-diisopropylcarbodiimide, hydroxybenzotriazole and diisopropylethylamine was added. Then the peptide resin was washed with dimethylformamide (3×2 ml) and Fmoc protective group was removed by 20% solution of piperidine in dimethylformamide (2×2 ml, 5 min and 20 min) followed by washing with dimethylformamide (4×2 ml).

Step 6: Preparation of Ac-D-Nal-D-Cpa-D-Pal-Ser(tBu)-Aph(Hor)-D-Aph(Cbm)-Leu-Lys(iPr, Boc)-Pro-D-Ala-Rink Resin Fmoc-Ser(tBu)-OH, Fmoc-D-Pal-OH, Fmoc-D-Cpa-OH and Fmoc-D-Nal-OH (three-fold excess respect to the loading of the resin) were activated by HBTU (150 mg, 0.4 mmol) in presence of diisopropylethylamine (136 µl, 0.67 mmol) and coupled to the resin in 50 min to get Fmoc-protected decapeptide. The intermediate Fmoc deprotections were carried out using 20% solution of piperidine in dimethylformamide (2×2 ml, 5 min and 20 min) followed by washing with dimethylformamide (4×2 ml). Upon completion of the synthesis N-terminal amino group was acetylated with the mixture of acetic acid (23 µl, 0.4 mmol), diisopropylcarbodiimide (60 µl, 0.39 mmol), hydroxybenzotriazole (52 mg, 0.39 mmol) and diisopropylethylamine (114 µl, 0.65 mmol), peptide resin was washed with dimethylformamide (2×2 ml), dichloromethane (2×2 ml) and dried.

Step 7: Cleavage of Degarelix From the Resin

Dry peptide resin was suspended in 4 ml of the mixture of 1% water in trifluoroacetic acid and stirred for 1.5 hours. Then the resin was filtered and washed with 1 ml of trifluoroacetic acid. The organic solutions were collected and dried in vacuo. The solid residue was washed with methyl t-butyl ether and dried to get crude degarelix with overall yield 100 mg (50%) and HPLC purity 70%.

Example 2

Preparation of Degarelix Via Solid Phase Synthesis

Step 1: Preparation of Ac-D-Nal-D-Cpa-D-Pal-Ser(tBu)-Phe(p-NO₂)-D-Aph(Cbm)-Leu-Lys(iPr, Boc)-Pro-D-Ala-Rink Resin Synthesis of the protected peptide was carried out by step-by-step solid phase peptide synthesis using Rink amide resin (3 g, loading 0.65 mmol/g). After swelling of the resin in 12 ml of dimethylformamide Fmoc protective group was removed by 20% solution of piperidine in dimethylformamide (2×12 ml, 5 min and 15 min) and the resin was washed with dimethylformamide (4×12 ml). Fmoc-D-Ala-OH, Fmoc-Pro-OH, Fmoc-Lys(iPr, Boc)-OH, Fmoc-Leu-OH, Fmo c-D-Aph(Cbm)-OH, Fmoc-Phe(p-NO₂), Fmoc-Ser(tBu)-OH, Fmoc-D-Pal-OH, Fmoc-D-Cpa-OH, Fmoc-D-Nal-OH (three-fold excess respect to the loading of the resin and two-fold excess in case of Fmoc-Lys(iPr, Boc)-OH) were activated by HBTU (2.2 g, 5.8 mmol) in presence of diisopropylethylamine (1.7 ml, 9.8 mmol) and coupled to the resin in 60 min. The solution was filtered off and the resin was washed with dimethylformamide (3×12 ml). After each coupling the unreacted amino groups, as well as the N-terminal amino group, were capped using a solution of acetic anhydride (0.54 ml) and diisopropylethylamine (0.93 ml) in 10.5 ml of dimethylformamide.

Step 2: Preparation of Ac-D-Nal-D-Cpa-D-Pal-Ser(tBu)-Aph-D-Aph(Cbm)-Leu-Lys(iPr, Boc)-Pro-D-Ala-Rink resin The obtained peptide resin was treated with a solution of tin (II) chloride dihydrate (4.4 g, 0.019 mol) and diisopropylethylamine (0.4 ml, 2.3 mmol) in 12 ml of dimethylformamide for 10 hours. At the end of the reaction the solvent was filtered off and the resin was washed with dimethylformamide (3×12 ml).

Step 3: Preparation of Ac-D-Nal-D-Cpa-D-Pal-Ser(tBu)-Aph(Hor)-D-Aph(Cbm)-Leu-Lys(iPr, Boc)-Pro-D-Ala-Rink Resin A solution of dihydroorotic acid (0.62 g, 3.9 mmol), diisopropylcarbodiimide (0.6 ml, 3.9 mmol), 1-hydroxybenzotriazole (0.53 g, 3.9 mmol) in 18 ml of dimethylformamide was stirred for 30 min and added to the peptide resin. After 1.5 hours the solution was filtered off and a freshly prepared mixture of dihydroorotic acid, N,N-diisopropylcarbodiimide, hydroxybenzotriazole and diisopropylethylamine was added. After 1.5 hours the peptide resin was washed with dimethylformamide (3×12 ml), dichloromethane (3×12 ml) and dried in vacuo.

Step 4: Cleavage of the Peptide From the Resin

Dry peptide resin (5 g) was suspended in 30 ml of a mixture of 5% water and 95% trifluoroacetic acid and stirred for 1.5 hours. Then the resin was filtered off and the solution was stirred for 1.5 hours more. Methyl tert-buthyl ether (100 ml) cooled to 4° C. was added to the solution of the peptide and stirred for 90 min. The procedure was repeated again with the resin remained after the first cleavage. The combined suspensions were filtered and the peptide was dried in vacuo to get crude degarelix with overall yield 55% and HPLC purity 84%.

Example 3

Reduction of Fmoc-Phe(NO2)-Leu-Lys(iPr)-Pro-Ala-Resin

3.1. With Sodium Dithionite (DEG-001-18)

Stock solution for the reduction: Na$_2$S$_2$O$_4$ 1050 mg (5 mmol), K$_2$CO$_3$ 968 mg (7 mmol), TBAHS 170 mg (0.5 mmol) in 5 ml of water (Ref.: Tetrahedron Lett. 54 (2013) 2600-2603).

130 mg of peptidyl-resin (swelled in DCM)+0.5 ml of DCM+0.5 mL of stock solution, reaction 2 h, washings 3×1 ml of DCM/water (v/v 1:1), DMF, MeOH and DCM.

Cleavage with the mixture TFA/water 99/1.

Product: Fmoc-4-Aph-Leu-Lys(iPr)-Pro-Ala-NH2 (M=810)

Analytical Method

| | |
|---|---|
| Instrument | Agilent UPLC 1290 series + Agilent 6530 mass accuracy Q-TOF |
| Column | C8 Zorbax Eclipse plus Agilent 07/13R 4.6 × 50 mm 1.8-Micron PN 9599941-906 |
| Mobile phase A (FM A) | water + 0.1% TFA |
| Mobile phase B (FM B) | ACN + 0.07% TFA |
| Flow rate | 1 ml/min |
| Detection | 226 nm |
| Run time | 40 min |

| | |
|---|---|
| Column temperature | 30° C. |
| Gradient elution | 0 min-5% FM B, 1 min-5% FM B, 31 min-90% FM B, 36 min-90% FM B, 37 min-5%, 40 min-5% |

Figure 3:
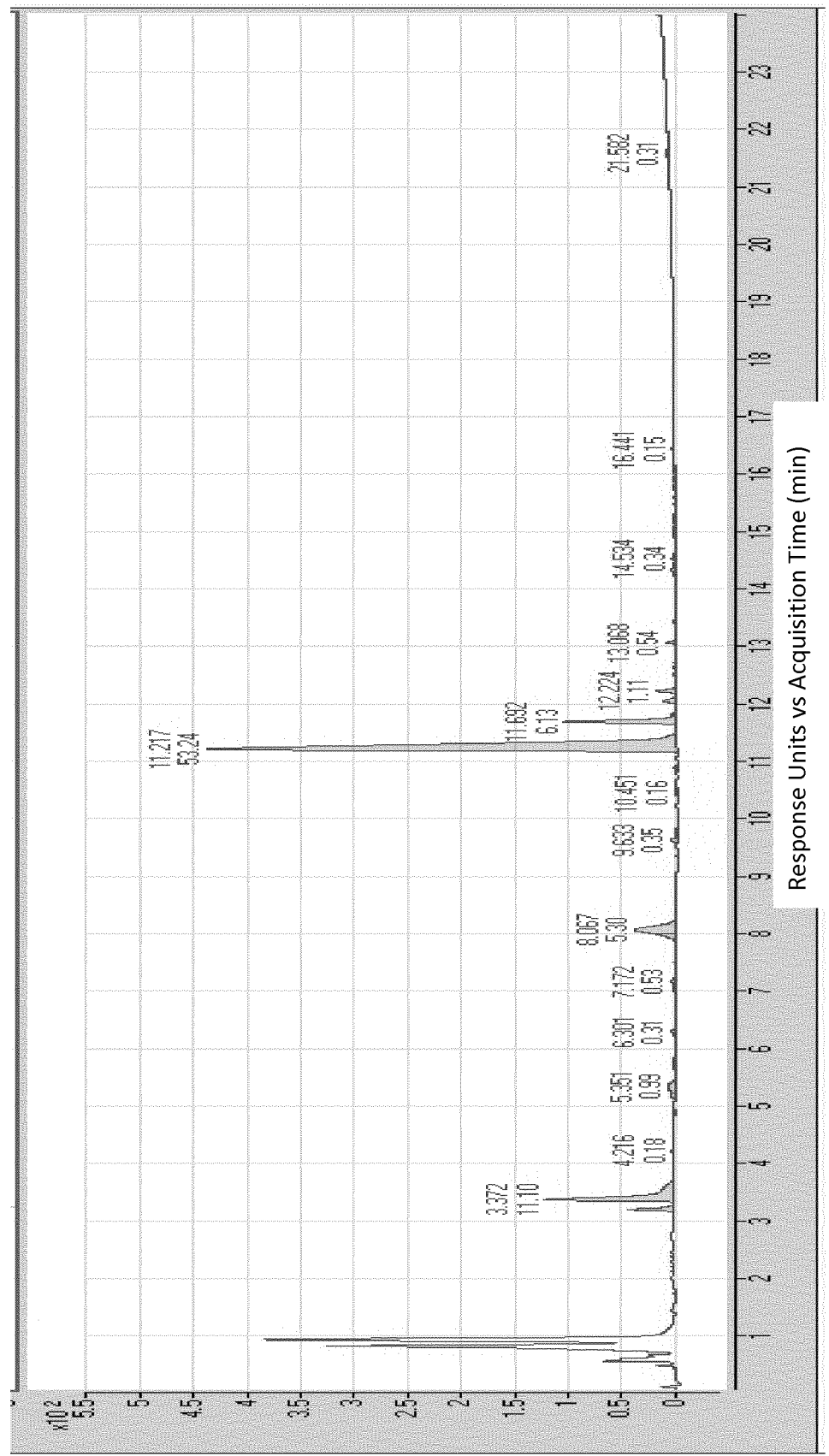
FIG. 3: This figure illustrates the HPLC profile of the pentapeptide after the reduction step with dithionite, according to example 3.1.

HPLC Result as Illustrated in FIG. 3

| Peak | RT | RRT | Area % |
|---|---|---|---|
| 1 | 3.20 | 0.29 | 2.13 |
| 2 | 3.37 | 0.30 | 12.08 |
| 3 | 8.07 | 0.72 | 7.16 |
| 4 | 11.22 | 1.00 | 57.52 |
| 5 | 11.42 | 1.02 | 0.43 |
| 6 | 11.69 | 1.04 | 6.67 |
| 7 | 12.05 | 1.07 | 0.92 |
| 8 | 12.22 | 1.09 | 1.25 |
| 9 | 13.07 | 1.16 | 0.61 |
| 10 | 24.09 | 2.15 | 2.53 |

Main peak (product): RT=11.22 min, purity 53.24%, [M+H]+=811.45

Main impurities: RT=3.15 min, [M+H]+=669.30 (−142, not identified)

RT=3.37, 11.10%, [M+H]+=589.38 (−222, -Fmoc)

RT=8.07, 5.30%, no TIC signal

RT=11.69, 6.13%, [M+H]+=891.40 (+90, not identified)

Results: The reduction is completed in 2 h, but partial Fmoc-deprotection occurs (17% respect to the quantity of the product)

3.2 With Tin(II)Chloride (DEG-001-35-2)

130 mg of peptidyl-resin was treated with a solution of tin (II) chloride dehydrate (0.19 g, 0.82 mmol) and diisopropylethylamine (30 μl, 0.16 mmol) in 2 ml of dimethylformamide for 10 hours. At the end of the reaction the solvent was filtered off and the resin was washed with dimethylformamide (2×2 ml) and DCM (2×2 ml).

Cleavage with the mixture TFA/water 99/1.

Product: Fmoc-4-Aph-Leu-Lys(iPr)-Pro-Ala-NH2 (M=810)

Figure 4:
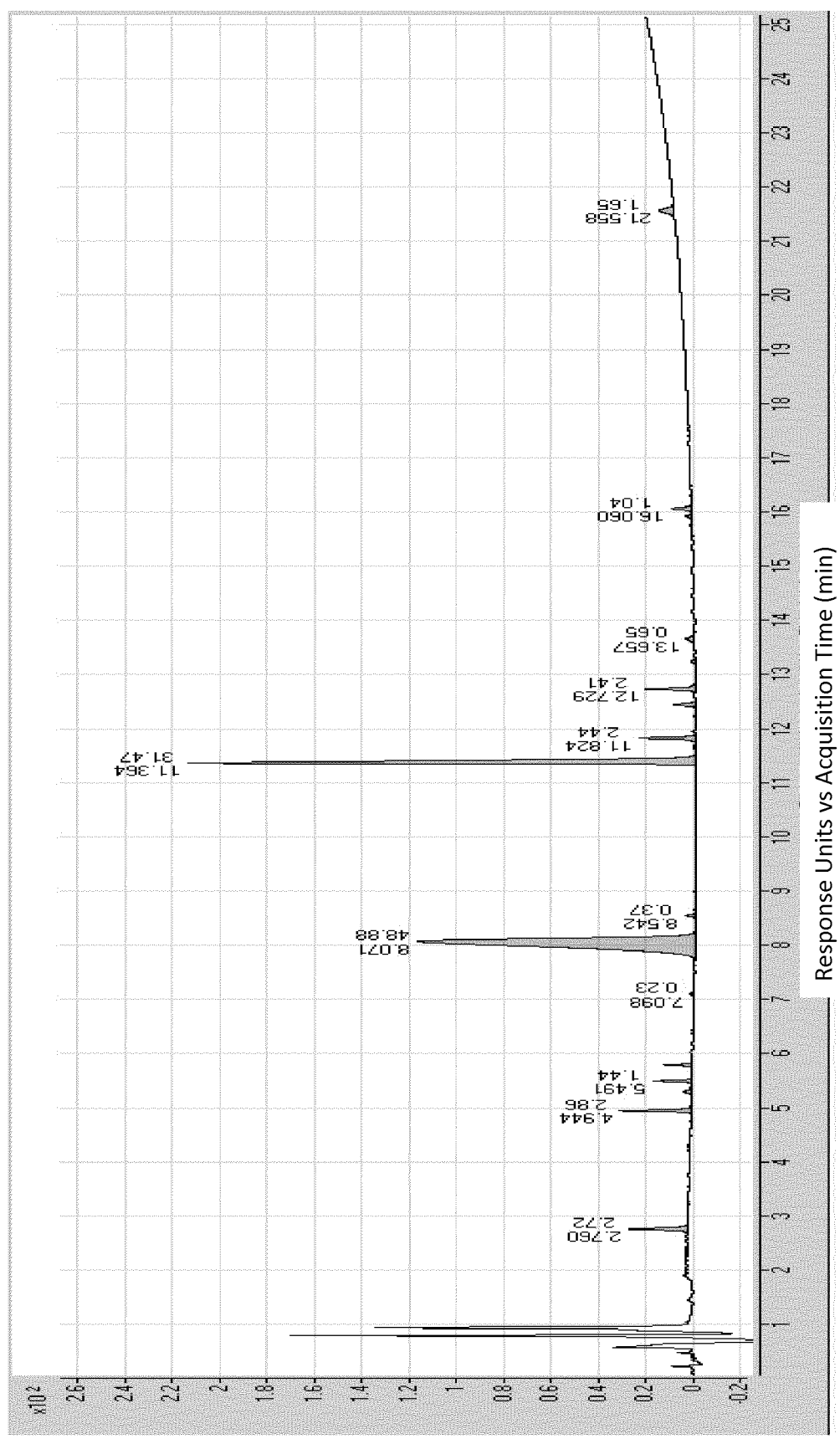
FIG. 4: This figure illustrates the HPLC profile of the pentapeptide after the reduction step with tin chloride, according to example 3.2.

HPLC Result as Illustrated in FIG. 4

No Fmoc-deprotected product was observed*

*the peak with rt 8.07 was seen in both cases. It do not give a TIC signal, probably, it is not a peptide impurity (salts or non-peptide organic compound). It was not taken into consideration while calculating HPLC purity.

Comparative Table

| Method of reduction | HPLC purity, % | Fmoc-deprotected product, % |
|---|---|---|
| Sodium dithionite | 65 | 17 |
| Tin (II) chloride | 67 | None |

The invention claimed is:

1. A compound of formula II

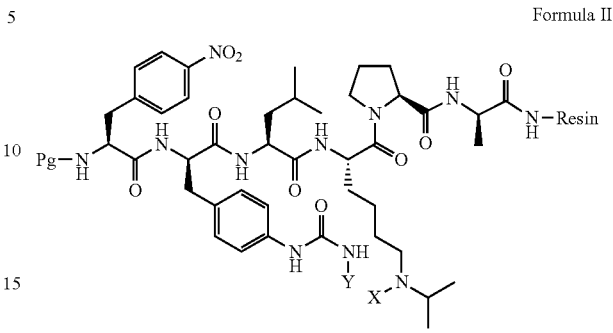

Formula II wherein Pg is a terminal protecting group or H, X and Y are side chain protecting groups or H, and Resin is a solid support, and wherein the compound is not attached to a solid support, the Resin is H.

2. A method for preparing the compound of formula II of claim 1, comprising the following steps:

a) reducing a compound of formula VII,

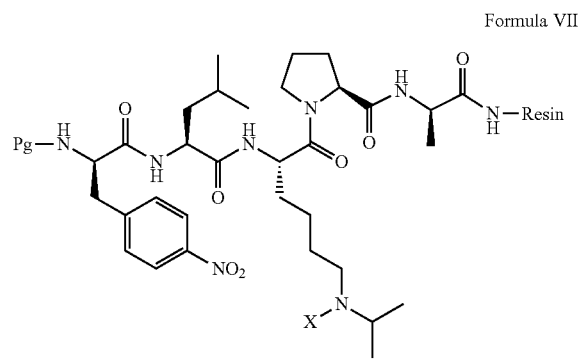

Formula VII wherein Pg is a terminal protecting group; X is a side chain protecting group, and Resin is a solid support with a reducing agent to form a compound of formula VIII,

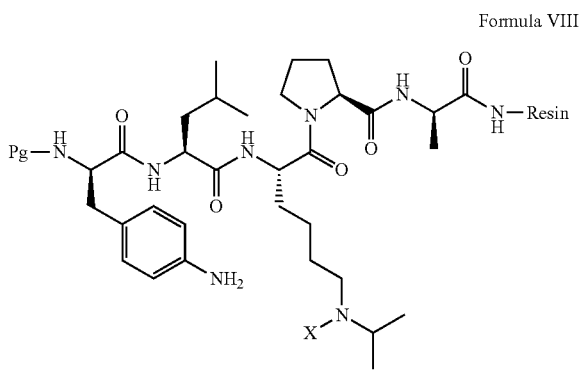

Formula VIII wherein Pg is a terminal protecting group; X is a side chain protecting group, and Resin is a solid support; and b) reacting the compound of formula VIII with alkyl isocyanate or alkali metal cyanate to form a compound of formula IX,

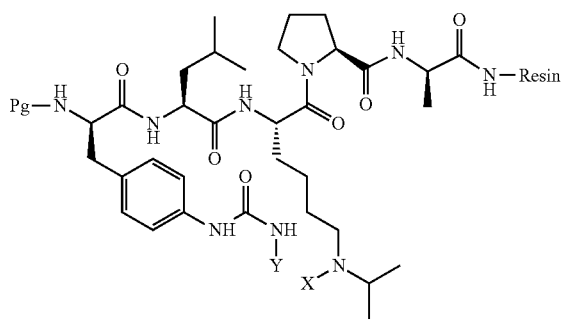

Formula IX wherein Pg is a terminal protecting group, X and Y are side chain protecting groups, wherein Y is H when an alkali metal cyanate is present, and Y is tBu or another alkyl group, when alkyl isocyanate is present and Resin is a solid support; and c) deprotecting the compound of formula IX to remove the terminal protecting group followed by coupling with the protected L-isomer of the amino acid of formula X,

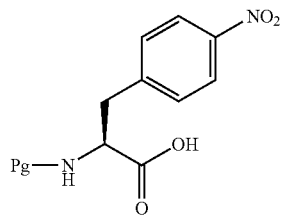

Formula X wherein Pg is a terminal protecting group, in the presence of a coupling reagent to form the compound of formula II.

3. The method according to claim 2, wherein preparing the compound of formula VII comprises the step of deprotecting the compound of formula XI,

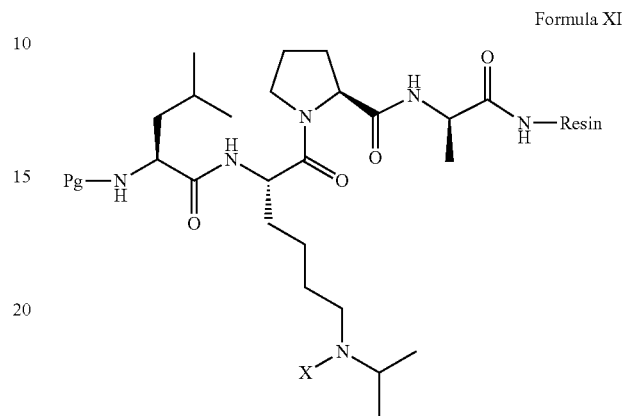

Formula XI wherein Pg is a terminal protecting group, X is a side chain protecting group and Resin is a solid support;

followed by a step of coupling the D isomer of the protected amino acid of formula X in the presence of a coupling reagent to form the compound of formula VII.

4. The method according to claim 2, wherein the terminal protection group Pg is the base-labile protective group Fmoc.

5. The method of claim 2, wherein said Pg group in step(c) is Fmoc.

6. A compound of formula V,

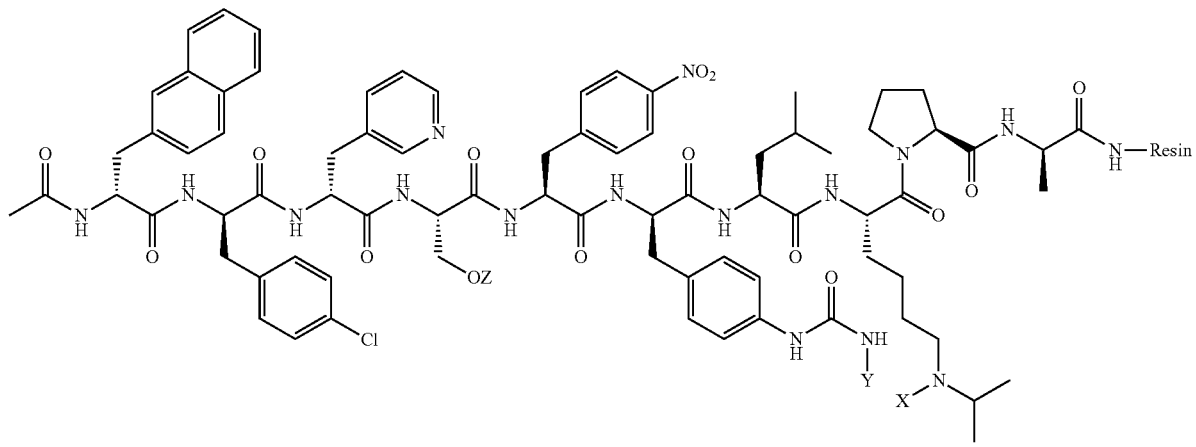

Formula V wherein X, Y and Z are side chain protecting groups or H, and Resin is a solid support and wherein the compound is not attached to a solid support the Resin is H.

7. A compound of formula VII,

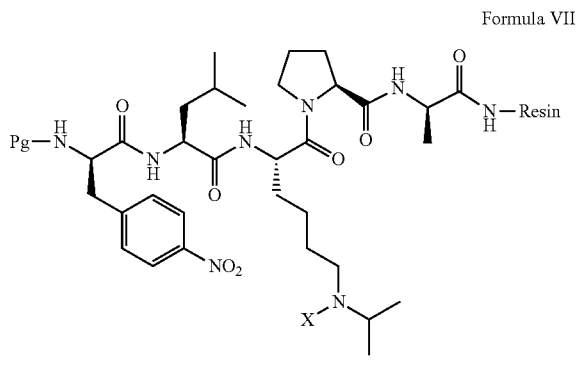

Formula VII wherein Pg is a terminal protecting group or H, X is a side chain protecting group or H, and Resin is a solid support and wherein the peptide is not attached to a solid support the Resin is H.

8. A method of synthesizing degarelix comprising converting a compound of formula II, a compound of formula V or a compound of formula VII into degarelix.

9. A method for preparing a decapeptide, wherein the decapeptide is characterized as being a peptide with at least one Aph derivative, in the $5^{th}$ position and one Aph derivative in the $6^{th}$ position in the decapeptide sequence, wherein the Aph derivative is selected from Aph(Hor) and Aph(Cbm), or a pharmaceutically acceptable salt thereof, wherein the method comprises the use of either p-nitrophenylalanine or a compound of formula X,

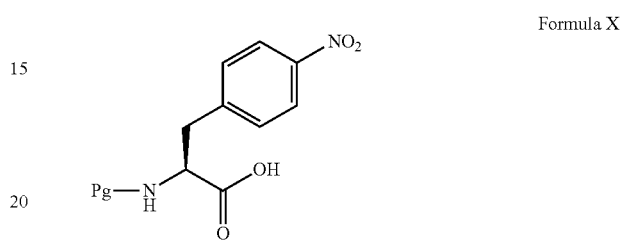

Formula X wherein Pg is a terminal protecting group; or a nitropeptide, wherein the decapeptide is degarelix of formula I,

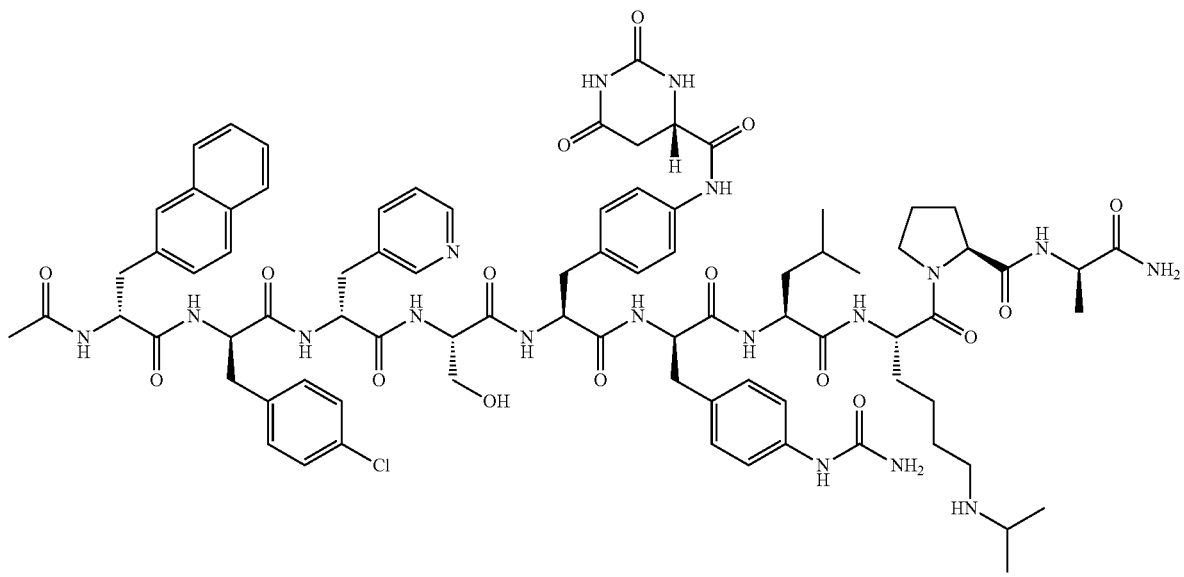

Formula I or a pharmaceutically acceptable salt thereof; and
wherein said nitro-peptide is a compound of formula II, V or VII

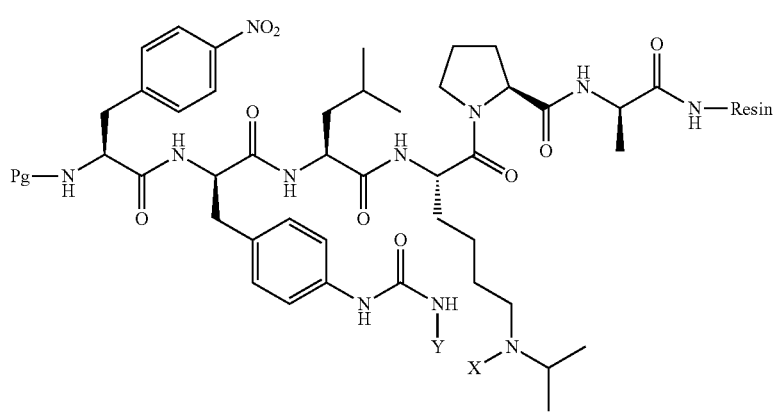

Formula II

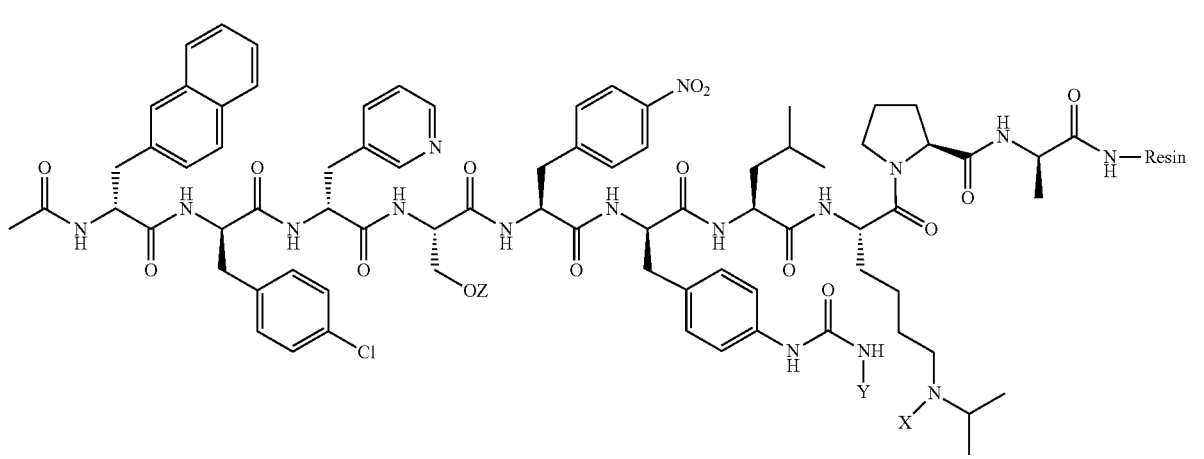

Formula V

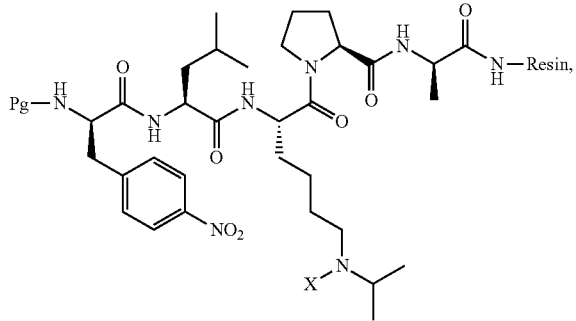

Formula VII wherein Pg is a terminal protecting group, X is a side chain protecting group and Y is a side chain protecting group or H, and Resin is H or a solid support.

10. The method according to claim 9, wherein the method comprises converting the compound of formula II into degarelix or a pharmaceutically acceptable salt thereof.

11. The method according to claim 9, wherein the method is performed as solid phase peptide synthesis.

12. The method according to claim 9, further comprising the steps of:
a) treating the compound of formula II with a reducing agent to form a compound of formula III, Formula III

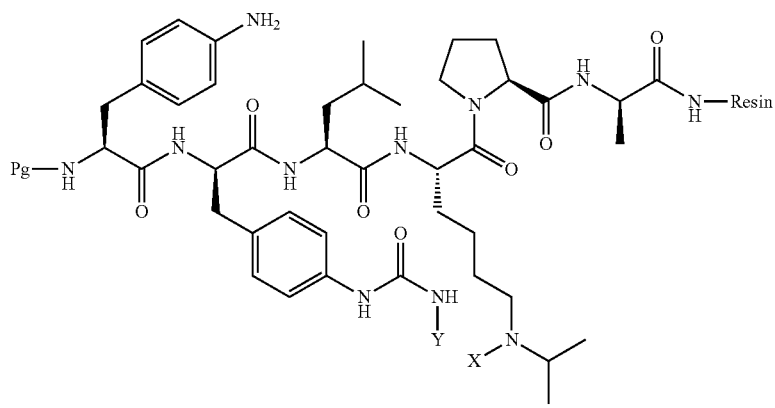

wherein Pg is a terminal protecting group, X is a side chain protecting group and Y is a side chain protecting group or H, and Resin is a solid support;

b) reacting the compound of formula III with an activated dihydroorotic acid to form a compound of formula IV, Formula IV

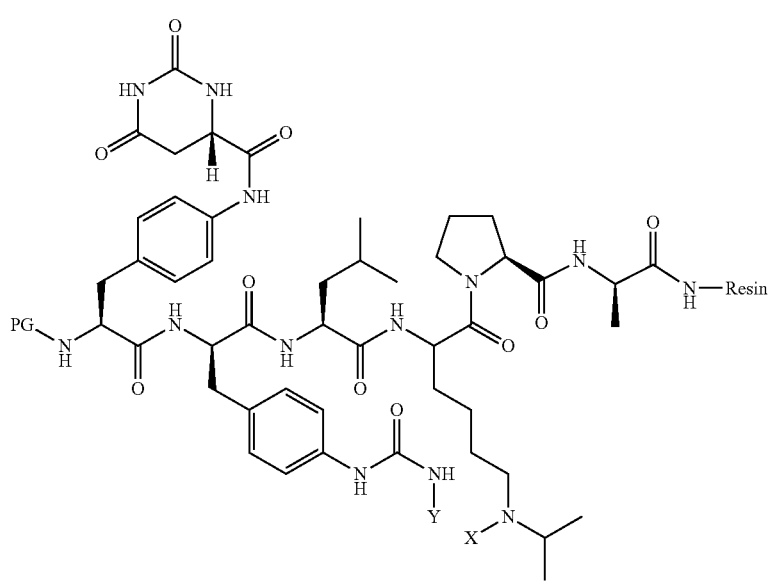

wherein Pg is a terminal protecting group, X is a side chain protecting group and Y is a side chain protecting group or H, and Resin is a solid support;

c) repeating the following steps (i)-(ii) attached to resin until a protected decapeptide is formed:
  (i) deprotecting the protected peptide to remove the terminal protecting group,
  (ii) coupling of the protected amino acid according to the order required by the degarelix sequence to the terminal amino group residue of the peptide attached to the resin using a coupling reagent to form a protected peptide, d) deprotecting the protected decapeptide to remove the terminal protecting group, e) acetylating the N-terminus of the resulting decapeptide in the presence of an acetylating agent, and f) cleaving the acetylated decapeptide from the resin to form degarelix or a pharmaceutically acceptable salt thereof;

thereby converting a compound of formula II into degarelix or a pharmaceutically acceptable salt thereof.

13. The method according to claim 9, comprising the steps of:

a) providing the compound of formula II, b) repeating the following steps (i)-(ii) until a protected decapeptide attached to resin is formed:
  (i) deprotecting the protected peptide attached to the resin to remove the terminal protecting group,
  (ii) coupling of the protected amino acid according to the order required by the degarelix sequence to the terminal amino group residue of the peptide attached to the resin using a coupling reagent to form a protected peptide attached to the resin;

c) deprotecting the protected decapeptide to remove the terminal protecting group, d) acetylating the N-terminus of the resulting decapeptide in the presence of an acetylating agent to result in a compound of formula V, Formula V

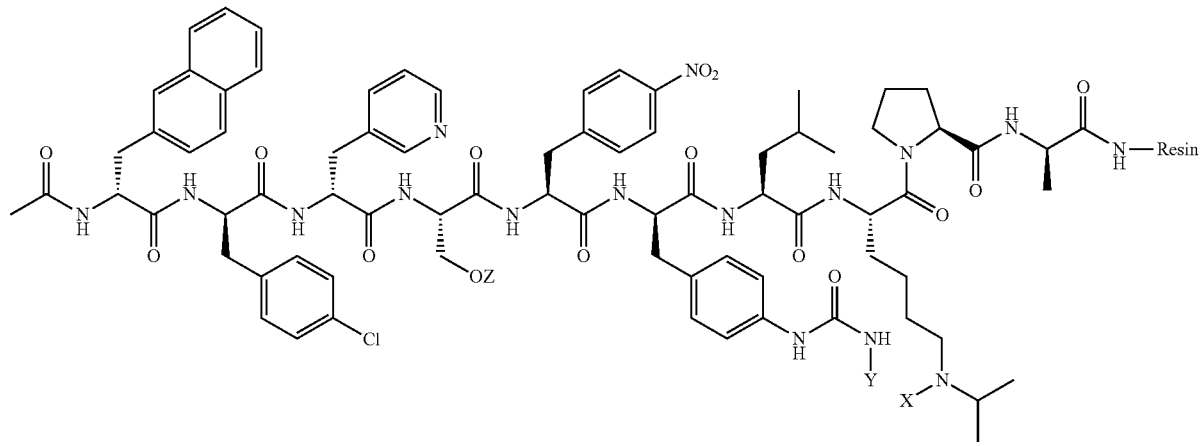

wherein X and Z are a side chain protecting group, Y is a side chain protecting group or H, and Resin is a solid support;

e) treating the compound of formula V with a reducing agent to form a compound of formula VI, Formula VI

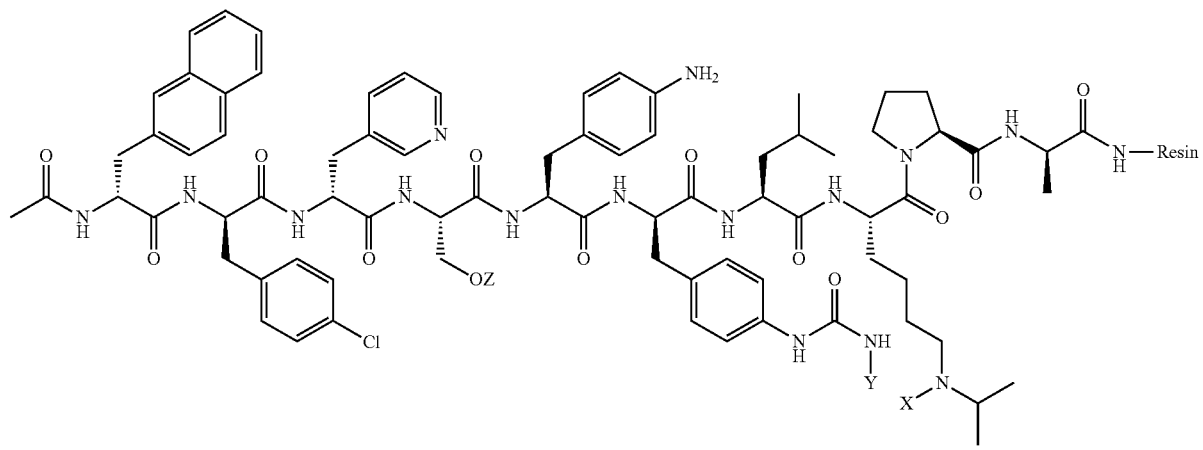

wherein X and Z are a side chain protecting group, Y is a side chain protecting group or H, and Resin is a solid support f) reacting the compound of formula VI with activated dihydroorotic acid to form a protected decapeptide attached to the resin; and g) cleaving the decapeptide from the resin to form degarelix or a pharmaceutically acceptable salt thereof.

14. The method according to claim 9, wherein the terminal protection group Pg is the base-labile protective group Fmoc.

* * * * *